United States Patent
Dowling et al.

(10) Patent No.: US 10,179,145 B2
(45) Date of Patent: *Jan. 15, 2019

(54) ADVANCED FUNCTIONAL BIOCOMPATIBLE POLYMERIC MATRIX USED AS A HEMOSTATIC AGENT AND SYSTEM FOR DAMAGED TISSUES AND CELLS

(71) Applicants: University of Maryland, Baltimore, Baltimore, MD (US); University of Maryland, College Park, College Park, MD (US)

(72) Inventors: Matthew Dowling, Washington, DC (US); John Hess, Baltimore, MD (US); Grant Bochicchio, Columbia, MD (US); Srinivasa Raghavan, Silver Spring, MD (US)

(73) Assignees: University of Maryland, College Park, College Park, MD (US); University of Maryland, Baltimore, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/001,215

(22) Filed: Jan. 19, 2016

(65) Prior Publication Data

US 2016/0206777 A1  Jul. 21, 2016

Related U.S. Application Data

(63) Continuation of application No. 14/595,542, filed on Jan. 13, 2015, now abandoned, and a continuation of application No. 14/595,551, filed on Jan. 13, 2015, now abandoned, said application No. 14/595,542 is a continuation of application No. 12/231,571, filed on Sep. 4, 2008, now Pat. No. 8,932,560, said application No. 14/595,551 is a continuation of application No. 12/231,571, filed on Sep. 4, 208, now Pat. No. 8,932,560.

(60) Provisional application No. 60/969,721, filed on Sep. 4, 2007.

(51) Int. Cl.

| | |
|---|---|
| A61K 31/722 | (2006.01) |
| A61K 47/56 | (2017.01) |
| A61K 47/61 | (2017.01) |
| A61L 27/20 | (2006.01) |
| A61L 26/00 | (2006.01) |
| A61K 9/127 | (2006.01) |
| A61K 9/70 | (2006.01) |
| A61K 47/69 | (2017.01) |

(52) U.S. Cl.
CPC .......... *A61K 31/722* (2013.01); *A61K 9/127* (2013.01); *A61K 9/1271* (2013.01); *A61K 9/7007* (2013.01); *A61K 47/56* (2017.08); *A61K 47/61* (2017.08); *A61K 47/69* (2017.08); *A61L 26/0023* (2013.01); *A61L 27/20* (2013.01); *A61L 2300/216* (2013.01); *A61L 2300/232* (2013.01); *A61L 2300/418* (2013.01); *A61L 2300/626* (2013.01); *A61L 2400/04* (2013.01); *A61L 2400/12* (2013.01)

(58) Field of Classification Search
None
See application file for complete search history.

(56) References Cited

U.S. PATENT DOCUMENTS

| | | | |
|---|---|---|---|
| 3,928,556 A * | 12/1975 | Sweger | ............... A61L 26/0014 424/45 |
| 4,394,373 A | 7/1983 | Malette et al. | |
| 4,532,134 A | 7/1985 | Malette et al. | |
| 4,572,906 A | 2/1986 | Sparkes et al. | |
| 4,752,466 A | 6/1988 | Saferstein et al. | |
| 4,895,724 A | 1/1990 | Cardinal et al. | |

(Continued)

FOREIGN PATENT DOCUMENTS

| | | |
|---|---|---|
| EP | 927053 | 4/2003 |
| EP | 1115747 | 2/2004 |

(Continued)

OTHER PUBLICATIONS

Neuffer et al. Mil Med. vol. 169 No. 9, pp. 716-720. publication year: 2004.*

(Continued)

*Primary Examiner* — Katherine Peebles

(74) *Attorney, Agent, or Firm* — The Morales Law Firm, LLC; Joseph L. Morales, Esq.

(57) ABSTRACT

A hemostatic tissue sealant sponge and a spray for acute wounds are disclosed. The sponge comprises hydrophobically modified polymers that anchor themselves within the membrane of cells in the vicinity of the wound. The seal is strong enough to substantially prevent the loss of blood inside the boundaries of the sponge, yet weak enough to substantially prevent damage to newly formed tissue upon recovery and subsequent removal of the sponge. In examples, the polymers inherently prevent microbial infections and are suitable for oxygen transfer required during normal wound metabolism. The spray comprises hydrophobically modified polymers that form solid gel networks with blood cells to create a physical clotting mechanism to prevent loss of blood. In an example, the spray further comprises at least one reagent that increases the mechanical integrity of the clot. In another example, the reagent prevents microbial infection of the wound.

12 Claims, 12 Drawing Sheets

(56) References Cited

U.S. PATENT DOCUMENTS

| | | | |
|---|---|---|---|
| 4,952,618 A * | 8/1990 | Olsen | A61F 13/023 523/105 |
| 5,243,094 A | 9/1993 | Borg | |
| 5,378,472 A * | 1/1995 | Muzzarelli | A61K 8/4913 424/401 |
| 5,426,182 A | 6/1995 | Jenkins et al. | |
| 5,623,064 A | 4/1997 | Vournakis et al. | |
| 5,624,679 A | 4/1997 | Vournakis et al. | |
| 5,836,970 A | 11/1998 | Pandit | |
| 5,900,479 A | 5/1999 | Glasser et al. | |
| 5,919,574 A | 7/1999 | Hoagland | |
| 6,140,089 A | 10/2000 | Aebischer et al. | |
| 6,162,241 A | 12/2000 | Coury et al. | |
| 6,200,595 B1 | 3/2001 | Motoyashiki et al. | |
| 6,344,488 B1 | 2/2002 | Chenite et al. | |
| 6,371,975 B2 | 4/2002 | Cruise et al. | |
| 6,447,802 B2 | 9/2002 | Sessions et al. | |
| 6,458,147 B1 | 10/2002 | Cruise et al. | |
| 6,536,448 B2 | 3/2003 | McDevitt et al. | |
| 6,548,081 B2 | 4/2003 | Sadozai et al. | |
| 6,602,952 B1 * | 8/2003 | Bentley | A61K 47/48215 514/44 R |
| 6,663,653 B2 | 12/2003 | Akerfeldt | |
| 6,706,690 B2 | 3/2004 | Reich et al. | |
| 6,806,260 B1 | 10/2004 | Hirofumi et al. | |
| 6,827,727 B2 | 12/2004 | Stalemark et al. | |
| 6,830,756 B2 | 12/2004 | Hnojewyj | |
| 6,864,245 B2 | 3/2005 | Vournakis et al. | |
| 6,890,344 B2 | 5/2005 | Levinson | |
| 6,899,889 B1 | 5/2005 | Hnojewyj et al. | |
| 6,949,114 B2 | 9/2005 | Hnojewyj et al. | |
| 6,958,325 B2 | 10/2005 | Domb | |
| 6,967,261 B1 | 11/2005 | Soerens et al. | |
| 6,994,686 B2 | 2/2006 | Cruise et al. | |
| 6,995,137 B2 | 2/2006 | You et al. | |
| 7,019,191 B2 | 3/2006 | Looney et al. | |
| 7,041,657 B2 | 5/2006 | Vournakis et al. | |
| 7,098,194 B2 | 8/2006 | Chenite et al. | |
| 7,115,588 B2 | 10/2006 | Vournakis et al. | |
| 7,247,314 B2 | 7/2007 | Hnojewyj et al. | |
| 7,279,001 B2 | 10/2007 | Addis et al. | |
| 7,288,532 B1 | 10/2007 | Payne et al. | |
| 7,318,933 B2 | 1/2008 | Hnojewyj | |
| 7,320,962 B2 | 1/2008 | Reich et al. | |
| 7,351,249 B2 | 4/2008 | Hnojewyj et al. | |
| 7,371,403 B2 | 5/2008 | McCarthy et al. | |
| 7,482,503 B2 | 1/2009 | Gregory et al. | |
| 7,514,249 B2 | 4/2009 | Gower et al. | |
| 7,820,872 B2 | 10/2010 | Gregory et al. | |
| 7,897,832 B2 | 3/2011 | McAdams et al. | |
| 7,981,872 B2 | 7/2011 | Hardy et al. | |
| 8,088,095 B2 | 1/2012 | Hissong et al. | |
| 8,106,030 B2 | 1/2012 | Hardy et al. | |
| 8,119,780 B2 | 2/2012 | Baker et al. | |
| 8,152,750 B2 | 4/2012 | Vournakis et al. | |
| 8,269,058 B2 | 9/2012 | McCarthy et al. | |
| 8,361,504 B2 | 1/2013 | Hen et al. | |
| 8,382,794 B2 | 2/2013 | Belhe et al. | |
| 8,414,925 B2 | 4/2013 | Freier | |
| 8,481,512 B2 | 7/2013 | Vournakis et al. | |
| 8,486,033 B2 | 7/2013 | Orgill et al. | |
| 8,530,632 B2 | 9/2013 | Tijsma et al. | |
| 8,535,477 B2 | 9/2013 | Ladet et al. | |
| 8,536,230 B2 | 9/2013 | Laurencin et al. | |
| 8,623,274 B2 | 1/2014 | Kirsch et al. | |
| 8,653,319 B2 | 2/2014 | Amery et al. | |
| 8,658,193 B2 | 2/2014 | Greenwald | |
| 8,658,775 B2 | 2/2014 | Baker et al. | |
| 8,664,199 B2 * | 3/2014 | Dowling | A61K 31/724 514/55 |
| 8,668,899 B2 * | 3/2014 | Dowling | A61L 24/0026 424/1.13 |
| 8,668,924 B2 | 3/2014 | McCarthy et al. | |
| 8,703,170 B2 | 4/2014 | Hedrich et al. | |
| 8,703,176 B2 | 4/2014 | Zhu et al. | |
| 8,715,719 B2 | 5/2014 | Roorda et al. | |
| 8,735,571 B2 | 5/2014 | DeCarlo et al. | |
| 8,741,335 B2 | 6/2014 | McCarthy | |
| 8,771,258 B2 | 7/2014 | Hedrich et al. | |
| 8,795,727 B2 | 8/2014 | Gong et al. | |
| 8,802,652 B2 | 8/2014 | Myntti et al. | |
| 8,809,301 B2 | 8/2014 | Athanasiadis et al. | |
| 8,828,050 B2 | 9/2014 | Gregory et al. | |
| 8,835,528 B2 | 9/2014 | Pravata | |
| 8,840,867 B2 | 9/2014 | Sophie et al. | |
| 8,920,514 B2 | 12/2014 | Gregory et al. | |
| 8,932,560 B2 * | 1/2015 | Dowling | A61K 47/4823 424/423 |
| 8,951,565 B2 | 2/2015 | McCarthy | |
| 8,975,387 B1 | 3/2015 | Venditti et al. | |
| 8,993,540 B2 | 3/2015 | Haggard et al. | |
| 9,004,918 B2 | 4/2015 | McAdams et al. | |
| 9,012,429 B2 | 4/2015 | Baker et al. | |
| 9,029,351 B2 | 5/2015 | Baker et al. | |
| 9,034,379 B2 | 5/2015 | Freier | |
| 9,044,488 B2 | 6/2015 | Subramaniam et al. | |
| 9,061,087 B2 | 6/2015 | Roberts et al. | |
| 9,066,885 B2 * | 6/2015 | Raghavan | A61K 9/127 |
| 9,114,172 B2 | 8/2015 | Rhee et al. | |
| 9,119,894 B2 | 9/2015 | Huang et al. | |
| 9,132,206 B2 | 9/2015 | McCarthy | |
| 9,139,664 B2 | 9/2015 | Finkielsztein et al. | |
| 9,192,574 B2 | 11/2015 | Medina et al. | |
| 9,198,997 B2 | 12/2015 | Myntti et al. | |
| 9,205,170 B2 | 12/2015 | Lucchesi et al. | |
| 9,226,988 B2 | 1/2016 | Kirsch et al. | |
| 9,259,357 B2 | 2/2016 | Kirsch et al. | |
| 9,333,220 B2 | 5/2016 | Tijsma et al. | |
| 9,364,578 B2 | 6/2016 | Zhu et al. | |
| 9,370,451 B2 | 6/2016 | Hardy et al. | |
| 9,375,505 B2 | 6/2016 | Hedrich et al. | |
| 9,616,088 B2 | 4/2017 | Diehn et al. | |
| 2002/0028181 A1 | 3/2002 | Miller et al. | |
| 2002/0068151 A1 | 6/2002 | Kim et al. | |
| 2004/0001893 A1 | 1/2004 | Stupp | |
| 2005/0038369 A1 | 2/2005 | Gregory et al. | |
| 2005/0147656 A1 | 7/2005 | McCarthy | |
| 2005/0181027 A1 | 8/2005 | Messinger | |
| 2006/0094060 A1 | 5/2006 | Jarhede et al. | |
| 2006/0167116 A1 | 7/2006 | Uchegbu et al. | |
| 2006/0269485 A1 | 11/2006 | Friedman et al. | |
| 2007/0055364 A1 | 3/2007 | Hossainy | |
| 2007/0148215 A1 | 6/2007 | Teslenko et al. | |
| 2008/0103228 A1 | 5/2008 | Falcone et al. | |
| 2008/0254104 A1 | 10/2008 | Raghavan | |
| 2009/0062849 A1 | 3/2009 | Dowling | |
| 2009/0192429 A1 | 7/2009 | Daniels et al. | |
| 2009/0226391 A1 | 9/2009 | Roberts et al. | |
| 2011/0052665 A1 | 3/2011 | Hardy et al. | |
| 2011/0217785 A1 | 9/2011 | Liu et al. | |
| 2012/0058970 A1 | 3/2012 | Dowling | |
| 2012/0252703 A1 | 10/2012 | Dowling | |
| 2014/0275291 A1 | 9/2014 | McGrath et al. | |

FOREIGN PATENT DOCUMENTS

| | | |
|---|---|---|
| EP | 1294414 | 3/2006 |
| EP | 1859816 | 9/2010 |
| EP | 1401352 | 3/2012 |
| EP | 2288744 | 7/2012 |
| EP | 2358412 | 7/2012 |
| EP | 2296637 | 4/2014 |
| EP | 2340002 | 3/2015 |
| EP | 2632502 | 5/2015 |
| EP | 2473203 | 7/2016 |

OTHER PUBLICATIONS

Kheirabadi BS et al. J Trauma. vol. 59, No. 1 pp. 25-34. publication year: 2005. (abstract only).*

Lee et al. Langmuir, vol. 21, pp. 26-33, publication year: 2005.*

(56) References Cited

OTHER PUBLICATIONS

Muzzarelli et al. Antimicrobial Agents and Chemotherapy. Oct. 1990, pp. 2019-2023.*
Alam, Hasan B., et al. Comparative Analysis of Hemostatic Agents in a Swine Model of Lethal Groin Injury, J. Trauma 54:1077-1082 (2003).
Allerbo et al., Simulation of lipid vesicle rupture induced by an adjacent supported lipid bilayer patch (Colloids and Surfaces B: Biointerfaces 2011, 82, 632-636).
Anderluh et al., Properties of Nonfused Liposomes Immobilized on an L1 Biacore Chip and Their Permeabilization by a Eukaryotic Pore-forming Toxin, Anal. Biochem. 344:43-52 (2005).
Angelova, M. I.; Dimitrov, D. S. "Liposome electroformation." Faraday Discuss. 1986, 81, 303-306.
Ankit R. Patel and Curtis W. Frank, Quantitative Analysis of Tethered Vesicle Assemblies by Quartz Crystal Microbalance with Dissipation Monitoring: Binding Dynamics and Bound Water Content, Langmuir 22(18):7587-7599 (2006).
Arnaud, F.; Teranishi, K.; Tomori, T.; Carr, W.; McCarron, R. "Comparison of 10 hemostatic dressings in a groin puncture model in swine." J. Vascular Surg. 2009, 50, 632-639.
Kheirabadi, B. S.; Scherer, M. R.; Estep, J. S.; Dubick, M. A.; Holcomb, J. B. "Determination of Efficacy of New Hemostatic Dressings in a Model of Extremity Arterial Hemorrhage in Swine." J. Trauma 2009, 67, 450-460.
Bochicchio, G.; Kilbourne, M.; Kuehn, R.; Keledjian, K.; Hess, J.; Scalea, T. "Use of a modified chitosan dressing in a hypothermic coagulopathic grade V liver injury model." Am. J. Surg. 2009, 198, 617-622.
Boukobza et al., Immobilization in Surface-Tethered Lipid Vesicles as a New Tool for Single Biomolecule Spectroscopy, J. Phys. Chem. B 105(48):12165-12170 (2001).
Brandenberg, Greg et al. Chitosan: A New Tropical Hemostatic Agent for Diffuse Capillary Bleeding in Brain Tissue, Neurosurgery 15(1): 9-13 (1984).
Burkatovskaya, Marina et al., Use of Chitosan Bandage to Prevent Fatal Infections Developing From Highly Contaminated Wounds in Mice, Biomaterials 27:4157-4164 (2006).
Champion, H. R.; Bellamy, R. F.; Roberts, C. P.; Leppaniemi, A. "A profile of combat injury." J. Trauma2003, 54, S13-S19.
Christensen, S. M.; Stamou, D. "Surface-based lipid vesicle reactor systems: fabrication and applications." Soft Matter 2007, 3, 828-836.
Chenite, A. et al "Rheological characterization of thermogelling chitosan/glycerol-phosphate solutions" Carbohydrate Polymers 46, 39-47 (2001).
Chiaki Yoshina-Ishii and Steven G. Boxer, Arrays of Mobile Tethered Vesicles on Supported Lipid Bilayers, J. Am. Chem. Soc. 125(13):3696-3697 (2003).
Kheirabadi, Bijan S. et al., Hemostatic Efficacy of Two Advanced Dressings in an Aortic Hemorrhage Model in Swine, J. Trauma Injury, Infection, and Critical Care, 59:25-35 (2005).
Cooper et al., A Vesicle Capture Sensor Chip for Kinetic Analysis of Interactions with Membrane-Bound Receptors, Anal. Biochem. 277:196-205 (2000).
Coster, Bag-On-Valve Series Offers Faster Filling and Better Drop Resistance. 2007. Downloaded from the world wide web on Jan. 18, 2012 <http://www.coster.com/news/eng/2007-10-18_AE_bov/AE_Manchester_BOV_eng.pdf.>.
D. D. Lasic and D. Papahadjopoulos, Liposomes Revisited, Science 267(5202):1275-1276 (1995).
Dan D. Lasic, Novel Applications of Liposomes, Trens in Biotechnology (TIBTECH) 16:307-321 (1998).
Deng, Y.; Wang, Y.; Holtz, B.; Li, J. Y.; Traaseth, N.; Veglia, G.; Stottrup, B. J.; Elde, R.; Pei, D. Q.; Guo, A.; Zhu, X. Y. "Fluidic and air-stable supported lipid bilayer and cell-mimicking microarrays." J. Am. Chem. Soc.2008, 130, 6267-6271.
Desbrieres et al., Hydrophobic Derivatives of Chitosan: Characterization and Rheological Behaviour, Biological Macromolecules, 19:21-28 (1996).
Dimitrievski et al., Influence of Lipid-Bilayer-Associated Molecules on Lipid-Vesicle Adsorption (Langmuir 2010, 26 (8), 5706-5714).
Dimitrievski et al., Simujlations of Lipid Vesicle Adsorption for Different Lipid mixtures (Langmuir 2008, 24, 4077-4091).
Doolittle, R. F. "Fibrinogen and fibrin." Annu. Rev. Biochem. 1984, 53, 195-229.
Dowling, M.B., et al. "A self-assembling hydrophobically modified chitosan capable of reversible hemostatic action."Biomaterials. May 2011 Vo. 31, pp. 3351-3357.
Durian, Douglas J., el al. "Making a frothy shampoo or beer." Physics Today. pp. 62-63. May 2010.
Ellis-Behnke, R. G.; Liang, Y. X.; You, S. W.; Tay, D. K. C.; Zhang, S. G.; So, K. F.; Schneider, G. E. "Nano neuro knitting: Peptide nanofiber scaffold for brain repair and axon regeneration with functional return of vision." Proc. Natl. Acad. Sci. U. S. A. 2006, 103, 5054-5059.
Ellis-Behnke, R. G.; Liang, Y.-X.; Tay, D. K. C.; Kau, P. W. F.; Schneider, G. E.; Zhang, S.; Wu, W.; So, K.-F. "Nano hemostat solution: Immediate hemostasis at the nanoscale." Nanomedicine 2006, 2, 207-215.
Esquenet et al.,Structural and Rheological Properties of Hydrophobically Modified Polysaccharide Associative Networks, Langmuir 20(9):3583-3592 (2004).
Fernandes et al., Electrochemically Induced Deposition of a Polysaccharide Hydrogel onto a Patterned Surface, Langmuir 19(10):4058-4062 (2003).
Fu et al., Protein stability in controlled-release systems, Nature Biotechnology 18:24-25 (2000).
GlaxoSmithKline. Bactroban Ointment: Prescribing Information. Research Triangle Park, NC, May 2005. Downloaded from the world wide web on Jan. 17, 2013 <https://www.gsksource.com/gskprm/htdocs/documents/BACTROAN-OINTMENTS.PDF>.
Gregory F. Payne and Srinivasa R. Raghavan, Chitosan: a Soft Interconnect for Hierarchical Assembly of Nano-scale Components, Soft Matter 3:521-527 (2007).
Kurth, Dirk G. and Thomas Bein. "Monomolecular Layers and Thin Films of Silane Coupling Agents by Vapor-Phase Adsorption on Oxidized Aluminum." J. Phys. Chem. 1992. 96. 6707-6712.
Hirano and Noishiki, The Blood Compatibility of Chitosan and N-Acylchitosans, J. Biochem. Materials Res. 413-417 (1985).
Hong et al., Two-step Membrane Binding by Equinatoxin II, a Pore-forming Toxin from the Sea Anemone, Involves an Exposed Aromatic Cluster and a Flexible Helix, J. Biol. Chem. 277(44):41916-41924 (2002).
Hook et al., Supported Lipid Bilayers, Tethered Lipid Vesicles, and Vesicle Fusion Investigated Using Gravimetric, Plasmonic, and Microscopy Techniques, Biointerphases 3(2) (Jun. 2008).
Jung et al., Quantification of Tight Binding to Surface-Immobilized Phospholipid Vesicles Using Surface Plasmon Resonance: Binding Constant of Phospholipase A2, J. Am. Chem. Soc. 122(17):4177-4184 (2000).
Kaler et al., Phase Behavior and Structures of Mixtures of Anionic and Cationic Surfactants, J. Phys. Chem. 96(16): 6698-6707 (1992).
Kaler et al., Spontaneous Vesicle Formation in Aqueous Mixtures of Single-Tailed Surfactants, Science 245(4924): 1371-1374 (1989).
Kauvar, D. S.; Lefering, R.; Wade, C. E. "Impact of hemorrhage on trauma outcome: An overview of epidemiology, clinical presentations, and therapeutic considerations." J. Trauma 2006, 60, S3-S9.
Kean, T.; Thanou, M. "Biodegradation, biodistribution and toxicity of chitosan." Adv. Drug Deliv. Rev. 2010,62, 3-11.
Khan et al., Mechanical, Bioadhesive Strength and Biological Evaluations of Chitosan Films for Wound Dressing, J. Pharm Pharmaceut. Sci. 3(3):303-311 (2000).
Kim, Seung-Ho MD; Stezoski, S. William; Safar, Peter MD; Capone, Antonio MD; Tisherman, Samuel MD. "Hypothermia and Minimal Fluid Resuscitation Increase Survival after Uncontrolled Hemorrhagic Shock in Rats" Journal of Trauma-Injury Infection & Critical Care. 42(2):213-222, Feb. 1997.
Kjoniksen et al., Light Scattering Study of Semidilute Aqueous Systems of Chitosan and Hydrophobically Modified Chitosans, Macromolecules 31(23):8142-8148 (1998).

(56) References Cited

OTHER PUBLICATIONS

Knoll, W.; Frank, C. W.; Heibel, C.; Naumann, R.; Offenhausser, A.; Ruhe, J.; Schmidt, E. K.; Shen, W. W.; Sinner, A. "Functional tethered lipid bilayers." J. Biotechnol. 2000, 74, 137-58.

Koehler et al., Microstructure and Dynamics of Wormlike Micellar Solutions Formed by Mixing Cationic and Anionic Surfactants, J. Phys. Chem. B 104(47):11035-11044 (2000).

Yoshina-Ishii et al. "General Method for Modification of Liposomes for Encoded Assembly on Supported Bilayers." J. Am. Chem. Soc. 2005, 127, 1356-1357.

Kozen, Buddy G. et al., An Alternative Hemostatic Dressing: Comparison of CELOX, HemCon, and QuikClot, Acad. Emerg. Med. 15:74-81(2008).

Kubota, et al. Gelation Dynamics and Gel Structure Fibrinogen, Colloids Surf. B. Biointerfaces 38:103-109 (2004).

Kumar, R.; Raghavan, S. R. "Thermothickening in solutions of telechelic associating polymers and cyclodextrins." Langmuir 2010, 26, 56-62.

Larson, M. J.; Bowersox, J. C.; Lim, R. C.; Hess, J. R. "Efficacy of a fibrin hemostatic bandage in controlling hemorrhage from experimental arterial injuries." Arch. Surg. 1995, 130, 420-422.

Lee et al., Transition from Unilamellar to Bilamellar Vesicles Induced by an Amphiphilic Biopolymer, Phys. Review Letters, 96:048102-1-048102-4 (2006).

Lee et al., Vesicle-Biopolymer Gels: Networks of Surfactant Vesicles Connected by Associating Biopolymers, Langmuir 21(1):26-33 (2005).

Lew, W. K.; Weaver, F. A. "Clinical use of topical thrombin as a surgical hemostat." Biologics 2008, 2, 593-599.

Li et al., Multivesicular Liposomes for Oral Delivery of Recombinant Human Epidermal Growth Factor, Arch Pharm Res 28(8):988-994 (2005).

Lu, S. et al. "Preparation of Water-Soluble Chitosan" Journal of Applied Polymer Science 91, 3497-2503 (2004).

Lunelli et al., Covalently Anchored Lipid Structures on Amine-Enriched Polystyrene, Langmuir 21(18):8338-8343 (2005).

Macfarlane, R. G. "An enzyme cascade in the blood clotting mechanism, and its function as a biological amplifier." Nature 1964, 202, 498-499.

Malette, William G. et al. Chitosan: A New Hemostatic, The Annals of Thoracic Surgery 36(1):55-58 (1983).

Mansur Yalpani and Laurence D. Hall, Some Chemical and Analytical Aspects of Polysaccharide Modifications. Formation of Branched-Chain, Soluble Chitosan Derivatives, Macromolecules 17(3):272-281 (1984).

Mathivet et al., Shape Change and Physical Properties of Giant Phospholipid Vesicles Prepared in the Presence of an AC Electric Field, Biophysical Journal 70:1112-1121 (1996).

Meier, Wolfgang et al., Vesicle and Cell Networks: Interconnecting Cells by Synthetic Polymers, Langmuir 12:5028-5032 (1996).

Michael I. Fisher and Torbjorn Tjarnhage, Structure and Activity of Lipid Membrane Biosensor Surfaces Studied with Atomic Force Microscopy and a Resonant Mirror, Biosensors & Bioelectronics 15:463-471 (2000).

Naumann et al., Proton Transport Through a Peptide-tethered Pilayer Lipid Membrane by the H+-ATP Synthase from Chloroplasts Measured by Impedance Spectroscopy, Biosensors and Bioelectronics 17:25-34 (2002).

Naumann, C. A.; Prucker, O.; Lehmann, T.; Ruhe, J.; Knoll, W.; Frank, C. W. "The polymer-supported phospholipid bilayer: Tethering as a new approach to substrate-membrane stabilization." Biomacromolecules2002, 3, 27-35.

Neuffer, M. C.; McDivitt, J.; Rose, D.; King, K.; Cloonan, C. C.; Vayer, J. S. "Hemostatic dressings for the first responder: A review." Military Med. 2004, 169, 716-720.

New I Pioneer Chip L1 Improved binding studies in model membrane systems, BIA Journal No. 2 1998.

Nikolelis et al., A Minisensor for the Rapid Screening of Sucralose Based on Surface-stabilized Bilayer Lipid Membranes, Biosensors & Bioelectronics 15:439-444 (2000).

Paul S. Cremer and Steven G. Boxer, Formation and Spreading of Lipid Bilayers on Planar Glass Supports, J. Phys. Chem. B 103(13):2554-2559 (1999).

Pusateri, A. E.; Holcomb, J. B.; Kheirabadi, B. S.; Alam, H. B.; Wade, C. E.; Ryan, K. L. "Making sense of the preclinical literature on advanced hemostatic products." J. Trauma 2006, 60, 674-682.

Puu et al., Retained Activities of Some Membrane Proteins in Stable Lipid Bilayers on a Solid Support, Biosensors and Bioelectronics 10:463-476 (1995).

Raghavan, S. R.; Cipriano, B. H. Gel formation: Phase diagrams using tabletop rheology and calorimetry. InMolecular Gels; Weiss, R. G., Terech, P., Eds.; Springer: Dordrecht, 2005; pp. 233-244.

Rao, S. B.; Sharma, C. P. "Use of chitosan as a biomaterial: Studies on its safety and hemostatic potential." J. Biomed. Mater. Res. 1997, 34, 21-28.

Redepenning, J. et al. "Electrochemical preparation of chitosan/hydroxyapatite composite coatings on titanium substrates." Journal of Biomedical Materials Research. vol. 66A. pp. 411-416. 2003.

Reiss, R. F.; Oz, M. C. "Autologous fibrin glue: Production and clinical use." Transfusion Med. Rev. 1996, 10, 85-92.

Rodriguez, M.S., et al "Interaction between chitosan and oil under stomach and duodenal digestive chemical conditions" Biosci. Biotechnol. Biochem. 69 (11), 2057-2062 (2005).

Rongen et al., Liposomes and Immunoassays, J. Immunol. Methods 204:105-133 (1997).

Tonelli, A. E. "Nanostructuring and functionalizing polymers with cyclodextrins." Polymer 2008, 49, 1725-1736.

Stavroula Sofou and James L. Thomas, Stable Adhesion of Phospholipid Vesicles to Modified Gold Surfaces, Biosensors and Bioelectronics 18:445-455 (2003).

Stewart, R. M.; Myers, J. G.; Dent, D. L.; Ennis, P.; Gray, G. A.; Villarreal, R.; Blow, O.; Woods, B.; McFarland, M.; Garavaglia, J.; Root, H. D.; Pruitt, B. A. "Seven hundred fifty-three consecutive deaths in a level 1 trauma center: The argument for injury prevention." J. Trauma 2003, 54, 66-70.

Szejtli, J. "Introduction and general overview of cyclodextrin chemistry." Chem. Rev. 1998, 98, 1743-1753.

Szymanska et al., Fullerene Modified Supported Lipid Membrane as Sensitive Element of Sensor for Odorants, Biosensors & Bioelectronics 16:911-915 (2001).

Tanaka, M.; Sackmann, E. "Polymer-supported membranes as models of the cell surface." Nature 2005,437, 656-663.

Tangpasuthadol, Surface Modification of Chitosan Films. Effects of Hydrophobicity on Protein Adsorption, Carbohydrate Res. 338:937-942 (2003).

Tanweer A. Khan and Kok Khiang Peh, A Preliminary Investigation of Chitosan Film as Dressing for Punch Biopsy Wound in Rats, J. Pharm. Pharmaceut. Sci. 6(1):20-26 (2003).

U.S. Office Action issued in related U.S. Appl. No. 12/077,173 dated Nov. 8, 2010.

U.S. Office Action issued in related U.S. Appl. No. 12/077,173 dated Apr. 14, 2011.

U.S. Office Action issued in related U.S. Appl. No. 12/231,571 dated Mar. 5, 2012.

U.S. Office Action issued in related U.S. Appl. No. 12/946,818 dated Jan. 28, 2013.

U.S. Notice of Allowance issued in related U.S. Appl. No. 12/946,818 dated Oct. 29, 2013.

U.S. Office Action issued in related U.S. Appl. No. 13/209,399 dated Mar. 1, 2013.

U.S. Office Action issued in related U.S. Appl. No. 13/310,579 dated Apr. 11, 2013.

Zhu et al., Reversible Vesicle Restraint in Response to Spatiotemporally Controlled Electrical Signals: A Bridge between Electrical and Chemical Signaling Modes, Langmuir 23(1)286-291 (2007).

Whang, Hyun Suk et al., Hemostatic Agents Derived from Chitin and Chitosan, J. Macromolecular Science 45:309-323 (2005).

Wu et al., Spatially Selective Deposition of a Reactive Polysaccharide Layer onto a Patterned Template, Langmuir 19 (3):519-524 (2003).

Wu et al., Voltage-Dependent Assembly of the Polysaccharide Chitosan onto an Electrode Surface, Langmuir 18 (22):8620-8625 (2002).

(56) References Cited

OTHER PUBLICATIONS

Yoshina-Ishii et al., Diffusive Dynamics of Vesicles Tethered to a Fluid Supported Bilayer by Single-Particle Tracking, Langmuir 22(13):5682-5689 (2006).
Zhang, Jing. Drug Delivery: Self-Assembled Nanoparticles based on Hydrophobically Modified chitosan as Carriers for Doxorubicin, Nanomedicine, Elsevier. Aug. 2007. pp. 258-265.
Zhdanov et al. Adsorption and Spontaneous Rupture of Vesicles Composed of Two Types of Lipids (Langmuir 2006, 22, 3477-3480).
Zhdanov et al., Comments on Rupture of Adsorbed Vesicles (Langmuir 2001, 17, 3518-3521).
Zhu et al., Bioinspired Vesicle Restraint and Mobilization Using a Biopolymer Scaffold, Langmuir 22(7):2951-2955 (2006).

* cited by examiner hydrophobes anchor and
remain anchored
in the bilayer of the
tissue/cell membrane

ADVANCED FUNCTIONAL BIOCOMPATIBLE POLYMERIC MATRIX USED AS A HEMOSTATIC AGENT AND SYSTEM FOR DAMAGED TISSUES AND CELLS

CROSS REFERENCE TO RELATED APPLICATION

This application is a continuation of U.S. patent application Ser. Nos. 14/595,542 and 14/595,551 filed on Jan. 13, 2015; which are continuations of U.S. patent application Ser. No. 12/231,571, filed on Sep. 4, 2008, now U.S. Pat. No. 8,932,560, which claims priority under 35 U.S.C. § 119 to the U.S. Provisional Application Ser. No. 60/969,721, filed on Sep. 4, 2007; which are all herein incorporated by reference in their entireties.

FIELD OF THE INVENTION

The present invention generally relates to the field of hydrophobically modified polymers and their use in promoting hemostasis in wounded tissues and cells.

BACKGROUND OF THE INVENTION

Currently, every year 21 million people worldwide suffer from serious injuries resulting in severe blood loss, and more than one third of these cases lead to death. (See Bledsoe, B. E. "The Golden Hour: Fact or Fiction." *Emergency Med. Serv.* 6, 105 (2002), which is herein incorporated by reference in its entirety.) Among these patients are American soldiers in Iraq whose fatality rate with severe injuries is 90%. Uncontrolled hemorrhaging from these injuries is the leading cause of preventable combat deaths among U.S. soldiers in Iraq. According to the Marine Corps registry, 45-60% of combat casualty deaths are due to potentially preventable uncontrolled hemorrhage. (See Clarke, Patrick E. "Z-Medica's Products Cited as Life Saving on Battlefield", which is herein incorporated by reference in its entirety.) Similarly, uncontrolled hemorrhage is the leading cause of potentially preventable deaths in the U.S. with 30-40% of all trauma deaths in the civilian population due to uncontrolled bleeding. In many cases, these deaths occur before the injured are able to be transported to medical treatment with approximately 40% of civilian and 90% of military casualties occurring before the patients reach a treatment facility. (See Kim, Seung-Ho M D; Stezoski, S. William; Safar, Peter M D; Capone, Antonio M D; Tisherman, Samuel M D. *Journal of Trauma-Injury Infection & Critical Care.* 42(2):213-222, February 1997, which is herein incorporated by reference in its entirety.) Many of these casualties can be prevented if an effective treatment is used to quickly stop the significant loss of blood.

Controlling hemorrhage is also a critical issue in medical facilities with 97 million patients experiencing surgical bleeding every year worldwide. (See B. S. Kheirabadi, E. M. Acheson, R. Deguzman, J. L. Sondeen, K. L. Ryan, A. Delgado, E. L. Dick, J. B. Holcomb, "Hemostatic efficacy of two advanced dressings in an aortic hemorrhage model in swine." *J. Trauma.* (2005), which is herein incorporated by reference in its entirety.) Despite advances in medical technology, hemorrhage control is still a major problem in emergency medical care. In the first 48 hours of hospitalization, approximately 51% of deaths are due to hemorrhage (See F W Verheugt, M J van Eenige, J C Res, M L Simoons, P W Serruys, F Vermeer, D C van Hoogenhuyze, P J Remme, C de Zwaan, and F Baer. Bleeding complications of intracoronary fibrinolytic therapy in acute myocardial infarction. Assessment of risk in a randomised trial, which is herein incorporated by reference it its entirety.)

Improving the ability to control hemorrhage for injuries that are otherwise survivable would greatly reduce trauma mortality, and this knowledge has encouraged numerous advancements in hemostatic control; however, the currently available hemostatic bandages are not sufficiently resistant to termination in high blood flow and they do not have strong enough adhesive properties to stop severe blood flow for an adequate time period.

Today the application of continuous pressure using gauze bandages remains the primary technique used to stanch blood flow, particularly in severe bleeding wounds. This procedure neither successfully nor safely stops severe blood flow. As in the past, this method continues to be a major survival problem in the case of serious life-threatening bleeding. Other currently available hemostatic bandages, such as collagen wound dressings or dry fibrin thrombin wound dressings do not have strong enough adhesive properties to serve any realistic purpose in the stanching of severe blood flow. These hemostatic bandages are also fragile and are therefore liable to fail if damaged due to bending or application of pressure. (See Gregory, Kenton W. and Simon J. McCarthy. Wound dressings, apparatus, and methods for controlling severe, life-threatening bleeding, which is herein incorporated by reference in its entirety.)

Recent advancement in hemostatic bandages have targeted the immediate treatment of acute wounds, such as the prevention of casualties due to hemorrhage on the battlefield. Chitosan based bandages have been approved and used in numerous settings including battlefield use with success. Chitosan is an amino-polysaccharide that is commercially produced from the deacetlyation of chitin which is an abundant natural biopolymer that is found in the exoskeleton of crustaceans. Advantages of chitosan as a material for wet wound dressings include its ability to accelerate wound-healing, its hemostatic properties, its stimulation of macrophage activity, and its general anti-microbial impact which helps prevent infection at the wound site. Chitosan is used as a hemostatic agent because of its cationic nature. Since the surfaces of most biological cells are anionic, including red blood cells, chitosan strongly adheres to the cells of tissue at wound sites because of an electrostatic interaction and is able to initially halt blood flow. (See Dornard, Alain and Monique. "Chitosan: Structure-Properties Relationship and Biomedical Applications." (2002), which is herein incorporated by reference it its entirety.)

Despite the advantages of using a chitosan-based dressing, there are also significant disadvantages. In a study conducted in 2005 by Kheirabadi et al, researchers caused injury to the aorta of pigs and attempted to control hemorrhage using the Hemostatic HemConÂ® Bandage. The results of the study showed that though the chitosan bandage effectively reached hemostasis immediately after its application, secondary bleeding resumed approximately 2 hours later and resulted in the death of the pigs. They found that the adhesion between the bandage and the tissue decreased as the bandaged became saturated with blood. (See B. S. Kheirabadi, E. M. Acheson, R. Deguzman, J. L. Sondeen, K. L. Ryan, A. Delgado, E. L. Dick, J. B. Holcomb, "Hemostatic efficacy of two advanced dressings in an aortic hemorrhage model in swine." *J. Trauma.* (2005), which is herein incorporated by reference in its entirety.) In realistic situations in which patients are incapable of reaching adequate medical treatment, such as on the battlefield, this time period is too short and the Hemostatic HemConÂ® Bandage would be an insufficient hemostatic agent.

Wound physiology is difficult to manipulate due to the complexity of cell-to-cell signaling networks which communicate during wound healing, but fortunately for healthy individuals, severe wounds can be healed quite well by simply disinfecting the wound area and stopping the loss of blood by suturing the open, damaged tissue. However, in many cases of acute wounds, internal or external, suturing is neither effective nor practical. In these cases, it is advantageous to use solid materials which adhere strongly enough to tissue such that they provide a seal upon pressing such materials onto the damaged tissue, thus preventing the loss of blood within the boundaries of the seal.

Additionally, blood clotting is a necessary aspect of wound physiology, and in many practical cases it is highly valuable for survival. However, for human beings and most mammals, the ability for blood to clot is limited because a significant increase in the ability of healthy mammalian organisms to form blood clots would most likely result in death of the organism as a result of any minor internal injury. In such cases, clots would form at the site of the injury, enter into the blood stream and eventually cause a stroke or heart failure due to blockage of important blood vessels. Because clotting ability must be limited under normal physiological conditions, in the case of acute wounds, which refers to a fast impact injury resulting in a high rate of blood loss, clotting is not a legitimate means to provide hemostasis. Therefore, acute wounds typically drain blood banks of their stocks as large blood transfusions are required to keep patients alive during transport to treatment facilities and subsequently during the surgery required to close the wound.

Therefore, it would be desirable to provide a strongly adhesive hemostatic bandage that promotes increased adhesion to wounded tissue or cells. It would also be desirable to provide a strongly adhesive flowable spray solution or surgical sealant to stop minor bleeding and to seal tissues in surgical applications.

SUMMARY OF THE INVENTION

Accordingly, the present invention provides a novel hybrid composition of matter that provides a strongly adhesive hemostatic agent. In a preferred exemplary embodiment, the composition of matter is a film or solid state tissue sealant sponge that is composed of a hydrophobically modified biopolymer matrix capable of hydrophobically interacting with tissue, particularly hemostatic interaction with damaged tissue. It is contemplated that this sponge may be included as part of a bandage or other applicator form as may be known by those skilled in the art. The hemostatic interaction occurs through a process wherein a plurality of short hydrophobic substituent, that are attached with the polymer backbone, interact with and adhere to the tissue.

In a further preferred exemplary embodiment, the composition of matter is formulated in a liquid state as a spray solution. The solution is composed, at least in part, of the hydrophobically modified biopolymer matrix capable of hydrophobically interacting with and/or gelling with cells, particularly a hemostatic interaction with tissue and/or red blood cells. Similar to the solid state film's interaction process, the hemostatic interaction of the solution occurs through a process wherein a plurality of short hydrophobic substituent, that are attached with the polymer backbone, interact with and adhere to the tissue and/or cells.

In other preferred exemplary embodiments, the current invention provides a system for delivering the novel solution including the functional capabilities of the hydrophobically modified polymer matrix. In one exemplary embodiment, the system includes a container for storing the solution and an ejection mechanism connected with the container to eject the solution to an environment outside the container. In an alternative exemplary embodiment the system includes two or more containers operationally connected through an ejection mechanism for ejecting a mixture of the solution and various other secondary components.

It is to be understood that both the foregoing general description and the following detailed description are exemplary and explanatory only and are not restrictive of the invention as claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous advantages of the present invention may be better understood by those skilled in the art by reference to the accompanying figures in which.

DETAILED DESCRIPTION OF THE INVENTION

Reference will now be made in detail to the presently preferred embodiments of the invention, examples of which are illustrated in the accompanying drawings.

Figure 1:
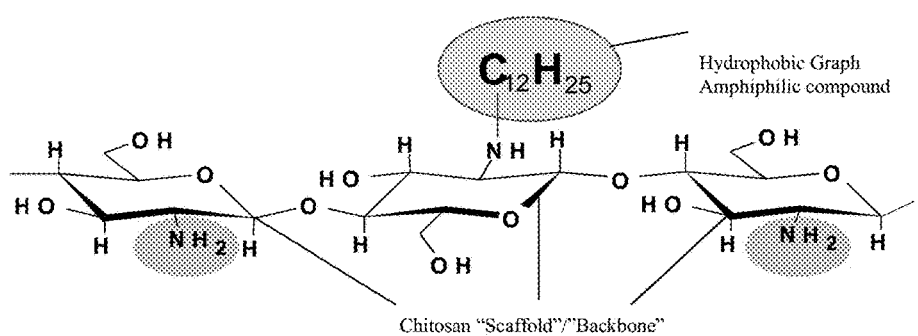
FIG. 1 is a structural and graphical illustration representing a readily reactive, hydrophobically modified chitosan matrix (hm-Chitosan), wherein the hm-Chitosan "backbone" or "scaffold" is capable of binding with a plurality of short hydrophobic substituents and the resulting compound being formulated as a tissue sealant sponge (solid state) or solution (liquid state) in accordance with an exemplary embodiment of the present invention.
Figure 2:
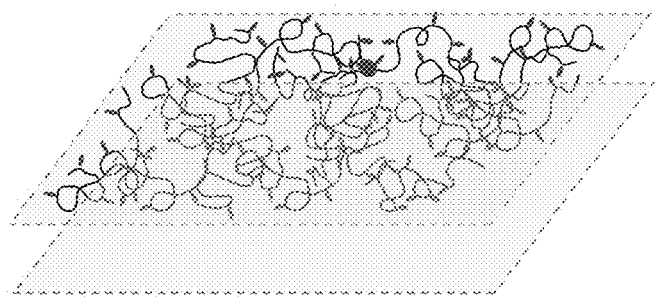
FIG. 2 is an illustration of a tissue sealant sponge showing the matrix including the plurality of short hydrophobic substituent that provide the hydrophobic interaction functional capability to the solid state and liquid state formulation of the current invention.
Figure 3:
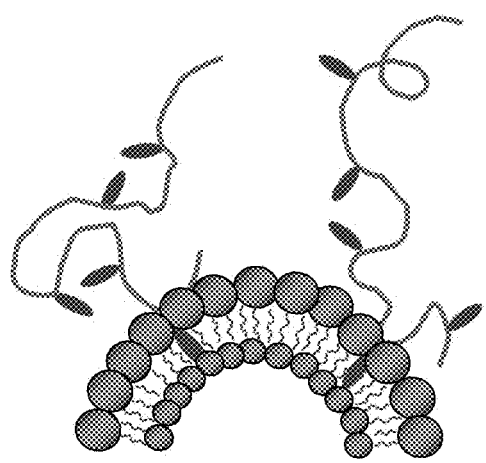
FIG. 3 is an illustration providing a representation of hydrophobic interaction between the short hydrophobic substituents of the modified polymer matrix and the bi-layer of tissue and/or cells.

Referring generally to FIGS. 1 and 2, the current invention provides a novel composition of matter that is capable of promoting hemostasis and/or hemostatic response through hydrophobic interactions with tissue and/or cells. In preferred embodiments, the current invention provides a hydrophobically modified polymer matrix capable of hydrophobic interactions with various tissue and/or cells to promote hemostasis. The hydrophobically modified polymer provides a readily reactive matrix and is capable of maintaining its reactive nature through various formulations, such as in a solid-state film or liquid state solution.

In a preferred embodiment, the current invention provides a solid state, hemostatic tissue sealant sponge that is composed of at least one polymer and a plurality of short hydrophobic substituents attached along the backbone of the polymer is disclosed. The sponge extends the hemostatic lifespan of a polymer-based bandage due to anchoring of the hydrophobic grafts into the membranes of cells in the vicinity of the damaged tissue. As a result, the sponge is an effective hemostatic sealant device. The level of hydrophobic modification of the polymer as well as hydrophobic substituent type is substantially optimized to develop materials which adhere to tissue in a manner idealized for clinical applications: the material comprising the sponge adheres strongly enough to provide hemostasis for a long enough time period to allow for substantially full patient recovery, yet weakly enough such that newly formed tissue is substantially undamaged upon removal of the tissue sealant device after patient recovery.

In another preferred embodiment, a hemostatic spray solution (liquid state) is composed of the hydrophobically modified polymer matrix providing at least one water-soluble polymer and a plurality of short hydrophobic substituent attached along the backbone of the polymer. The hydrophobically modified polymer sprayed in aqueous solution is able to form solid networks upon interaction with blood, as the hydrophobic substituent are able to anchor themselves within the bilayers of blood cell. The result is a localized "artificial clot" which physically prevents further blood loss around the newly formed solid network. "Artificial clots" herein refer to physical networks of hydrophobically modified polymers, blood cells, and surround tissue cells which effectively act as a solid barrier to prevent further blood loss. Additionally, the level of hydrophobic modification of the polymer as well as hydrophobic substituent type can be substantially optimized to yield rapidly forming and mechanically robust artificial clots. In an example, the hydrophobically modified polymer spray solution is mixed with at least one water-soluble reagent that results in faster and more efficient healing of the wound.

The novel hemostatic agent of the current invention is suitable for use with any various tissues and cells. These agents may be used with the tissues and cells of mammals. As used herein, the term "mammals" means any higher class of vertebrates that nourish their young with milk secreted by mammary glands, e.g. humans, rabbits and monkeys.

The polymer that forms the backbone of this reactive matrix is of synthetic or natural origin, including for example, water-soluble polysaccharides and water-soluble polypeptides. In particularly preferred embodiments, the polymer is one or more hydrophobically modified polysaccharides, including but not limited to cellulosics, chitosans and alginates, all of which are abundant, natural biopolymers. All three types of materials allow for the transfer of oxygen and moisture required to metabolize the wound healing physiology.

The natural origin of these polysaccharides varies, cellulosics are found in plants, whereas chitosans and alginates are found in the exoskeleton or outer membrane of a variety of living organisms. Many of these naturally occurring polymers, in addition to being able to form long stable chains for forming the backbone of the current invention, have other benefits that may promote further advantages for their use in environments of damaged tissue, hemorraghing, and/or exposed red blood cells. For instance, chitosan also has inherent anti-microbial properties; this is a crucial asset for materials covering open wounds because it eliminates the need to constantly change wound dressings in order to disinfect the wound manually between changes. Positive charges along the backbone of chitosan cause it to interact electrostatically with negatively charged blood cells, thus creating a sticky interface between a chitosan sponge and the wound. Chitosan provides hemostasis for an extended period of time when compared against standard bandages. For example, the sponge of the current invention provides substantially 30 minutes more absorption/adherence time before becoming saturated with blood cells and losing adhesion to the wound site.

The form of the natural polymers used may vary to include standard states, derivatives and other various formulations. For example, the cellulosics may include without limitation, hydroxyetyhl cellulose, hydroxypropyl cellulose, methyl cellulose, hydroxypropyl methyl cellulose, and/or hydroethyl methyl cellulose. Chitosans may include without limitation, the following chitosan salts: chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, chitosan glycolate and quaternary amine substituted chitosan and salts thereof. Alginates may include without limitation, sodium alginate, potassium alginate, magnesium alginate, calcium alginate, and/or aluminum alginate. It is to be understood that various other forms of any of these natural polysaccharides that provide the proper functional capabilities may be employed without departing from the scope and spirit of the present invention.

In alternative embodiments of this invention the polymeric component of the current invention is a mixture of polysaccharides. For instance, the mixture may be of various different sub-classes of a single polymer class. Alternatively, the mixture may include two or more different classes of polymer, for instance a cellolusic and a chitosan.

In a preferred embodiment, a matrix of the current invention is formed through the binding of numerous hydrophobically modified chitosan compounds, as shown in FIS. 1. These novel compounds consist of a biopolymer (e.g., chitosan) backbone that includes a hydrophilically reactive functional group (e.g., amino groups) that binds with the hydrophilically reactive head groups (e.g., carbonyl functional group) of an amphiphilic compound (e.g., aldehyde). The head group is further associated with a hydrophobic tail group. In the current embodiment, the hydrophobic tail may be for example a hydrocarbon. Thus, a hydrophobic tail is associated with the biopolymer's chitosan backbone providing the hydrophobic modification to the molecule that extends from the backbone and may interact with a surrounding environment in numerous ways, such as through hydrophobic interaction with other tissues, cells, molecules and/or structures. The hydrophobic interaction between the modified chitosan and the bi-layer of various tissues and/or cells occurs via the "insertion and anchoring" of the hydrophobic tail group of the short hydrophobic substituent into the bi-layer membrane of the tissues or cells. The insertion process is driven by the generally understood hydrophobic interaction and those forces that are at work which tend to group like molecules when they exist in a heterogenous environment. Thus, the hydrophobic effect or interaction is evidenced by the tendency of hydrophobic components to group together versus interacting or bonding with other molecules.

Typically, and for the purposes of the preferred embodiments of the instant application, these hydrophobically modified polymers (biopolymers) are referenced as being composed of a chitosan "backbone", "scaffold", and/or "lattice". Thus, the backbone of the hydrophobically modified biopolymer film matrix of the preferred embodiments of the current invention is the biopolymer chitosan. Other biopolymers, including but not limited to the cellulosics and alginates, which include similar characteristics of the chitosan backbone may be employed with departing from the scope and spirit of the instant invention.

Chitosan is a deacetylated derivative of chitin, wherein the degree of deacetylation (% DA) may range from 60-100% and determines the charge density. Chitosan is a linear polysaccharide composed of repeating β-(1-4)-linked D-glucosamine monomeric units.

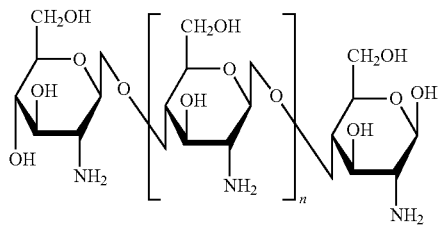

Chitosan structure showing three of the repeating beta-(1-4)-linked D-glucosamine units (deacetylated)

These repeating monomeric units include a free amino group (functional group) and may make molecules or compounds containing chitosan or its derivatives readily reactive. The hydrophic modification of the chitosan backbone is through the association of an amphiphilic compound with the amino group, such that the hydrophobic tail of the amphiphilic compound is bound with the hydrophilic backbone structure. As seen in FIGS. 1 and 2, this hydrophobically modified chitosan backbone (hm-Chitosan) may then be cast into a film. In the preferred embodiment of FIGS. 1 and 2, numerous hm-Chitosan backbones may fill a solution which may then be cast into a film forming the novel hm-Chitosan film of the current invention. This film matrix is a solid-state or dried film of the hm-Chitosan.

The formation or fabrication of the novel solid-state, hm-Chitosan matrix occurs through well known processes. The formation of the sponge of the current invention includes the formation step of freeze drying the solid state film of the matrix. Thus, a preferred embodiment of the current invention is a freeze dried, hm-Chitosan sponge or composition of matter which may be readily reactive with tissue, cells and additional molecules and/or compounds. The sponge composition of matter is prepared as a readily reactive, solid-state film matrix for application and use in damaged tissue adhesion and red blood cell gelling for promoting hemostasis. The sponge may be a bandage or included as part of a bandage that may be applied to a wounded area. However, various other implementation states of the current invention as may be contemplated by those of ordinary skill in the art are hereby assumed to fall within the scope of the current invention.

The sponge and spray solution of the current invention include at least one polymer and a plurality of short hydrophobic substituent attached along the backbone of the polymer. The short hydrophobic substituent preferably includes a hydrocarbon group having from about 8 to about 18 carbon atoms attached to the backbone of the at least one polymer. In preferred embodiments, the hydrocarbon group comprises an alkyl or arylalkyl group. As used herein, the term "arylalkyl group" means a group containing both aromatic and aliphatic structures. Examples of procedures for modifying polymers are as follows:

(1) Alginates can be hydrophobically modified by exchanging their positively charged counterions (e.g. $Na^+$) with tertiary-butyl ammonium ($TBA^*$) ions using a sulfonated ion exchange resin. The resulting TBA-alginate is dissolved in dimethylsulfoxide (DMSO) where reaction occurs between alkyl (or aryl) bromides and the carboxylate groups along the alginate backbone.

(2) Cellulosics can be hydrophobically-modified by first treating the cellulosic material with a large excess highly basic aqueous solution (e.g. 20 wt % sodium hydroxide in water). The alkali cellulose is then removed from solution and vigorously mixed with an emulsifying solution (for example, oleic acid) containing the reactant, which is an alkly (or aryl) halide (e.g. dodecyl bromide).

(3) Chitosans can be hydrophobically-modified by reaction of alkyl (or aryl) aldehydes with primary amine groups along the chitosan backbone in a 50/50 (v/v) % of aqueous 0.2 M acetic acid and ethanol. After reaction, the resulting Schiff bases, or imine groups, are reduced to stable secondary amines by dropwise addition of the reducing agent sodium cyanoborohydride.

The degree of substitution of the hydrophobic substituent on the polymer is from about 1 to about 30 moles of the hydrophobic substituent per mole of the polymer, which hydrophobic substitutions occur in up to 10% of available amines of the chitosan backbone, preferably between 1.5% and 4.5%. It is contemplated that more than one particular hydrophobic substituent is substituted onto the polymer, provided that the total substitution level is substantially within the ranges set forth above.

The short hydrophobic substituent is an amphiphilic compound meaning it is composed of a hydrophilic Head group and a hydrophobic Tail group. The Head group binds with the polymer and positions the Tail group to extend from the backbone of the polymer scaffold. This makes the hydrophobic Tail group available for hydrophobic interactions. The Tail group is preferably a hydrocarbon of various forms. As used herein, hydrocarbon(s) are any organic molecule(s) or compound(s) with a "backbone" or "skeleton" consisting entirely of hydrogen and carbon atoms and which lack a functional group. Thus, these types of compounds are hydrophobic in nature, unable to react hydrophilically, and therefore provide an opportunity for hydrophobic interaction. The hydrophobic interaction capability of the amphiphilic compound bound to the chitosan backbone may provide significant advantage to the current invention when compared to the prior art in that the interaction of the hydrophobically modified polymer matrix, whether chitosan, cellulosic or alginate based, with the bi-layer membrane of tissue(s) and cell(s) is a self-driven, thermodynamic process requiring less energy input. Thus, regardless of any particular form of the Tail group of the short hydrophobic substituent (amphiphilic compound), so long as it provides the opportunity for hydrophobic interaction with the tissue(s), cell(s), or other hydrophobically active molecules and/or compounds it falls within the scope and spirit of the current invention.

(1) Hydrocarbons, which are hydrophobic, may form into various types of compounds/molecules, such as gases (e.g. methane and propane), liquids (e.g., hexane and benzene), waxes or low melting solids (e.g., paraffin was and naphthalene), polymers (e.g., polyethylene, polypropylene and polystyrene), or biopolymers. Currently, hydrocarbons may be classified as follows:

(2) Saturated Hydrocarbons (alkanes) are composed entirely of single bonds between the carbon and hydrogen atoms and are denoted by (assuming non-cylcic structures) the general formula $C_nH_{2n+2}$. These types of compounds are the most simple of the hydrocarbons and are either found as linear or branched species of unlimited number.

(3) Unsaturated Hydrocarbons include one or more multiple bonds between carbon atoms of the compound, such as double bonds (alkenes-$C_nH_{2n}$) or triple bonds (alkynes-$C_nH_{2n-2}$). These multiple bonds create carbon atoms which are also commonly referred to as hydrogenated in that they are in need of the addition of further hydrogen atoms.

(4) Cycloalkanes consist of only carbon and hydrogen atoms are cyclic or "ring-shaped" alkane hydrocarbons denoted by the general formula $C_nH_{2(n+1-g)}$ where n=number of C atoms and g=number of rings in the molecule. Cycloalkanes are saturated because there are no multiple (double or triple) C—C bonds to hydrogenate (add more hydrogen to).

(5) Aromatic Hydrocarbons, also known as arenes, are hydrocarbons that contain at least one aromatic ring and may be denoted by the formula $C_nH_n$, wherein at a minimum n=6. Arenes (e.g., Benzene-$C_6H_6$) or Aromatic Hydrocarbons include a molecular structure which incorporates one or more planar sets of six carbon atoms connected by delocalized electrons numbering the same as if they consisted of alternating single and double covalent bonds.

From this basic classification system there exist many derivatives and further types of compounds that build therefrom. For example, numerous and varied compounds include more than one aromatic ring and are generally referred to as polyaromatic hydrocarbons (PAH); they are also called polycyclic aromatic hydrocarbons and polynuclear aromatic hydrocarbons. Various alternative/derivative forms of the saturated or unsaturated cycloalkanes, and aromatic hydrocarbons as are known and contemplated by those skilled in the art may be employed with the current invention and should be read as falling within the contemplated scope of the current invention.

Various types of other hydrophobic, organic compounds may generally include hydrocarbon backbones but may also include other types of atoms and/or incorporate/bind to other compounds/molecular structures that incorporate other types of atoms than just carbon and hydrogen. Thus, another classification system has developed by which organic compounds with generally hydrocarbon backbones but bound with other types of molecules may be separated, wherein such compounds may be designated either aromatic or aliphatic. Thus, compounds composed mainly, substantially or at least partially, but not exclusively of carbon and hydrogen may be divided into two classes:

1. aromatic compounds, which contain benzene and other similar compounds, and
2. aliphatic compounds (G. aleiphar, fat, oil), which do not.

In aliphatic compounds, carbon atoms can be joined together in straight chains, branched chains, or rings (in which case they are called alicyclic). They can be joined by single bonds (alkanes), double bonds (alkenes), or triple bonds (alkynes). Besides hydrogen, other elements can be bound to the carbon chain, the most common being oxygen, nitrogen, sulfur, and chlorine. Those of ordinary skill in the art will recognize that other molecules may also be bound to the carbon chains and that compounds of such heteroatomic structure are contemplated as falling within the scope of the current invention.

The hydrophobic Tail group of the amphiphilic compound bound to the polymer backbone of the current invention is capable of branching and/or allowing the inclusion of side chains onto its carbon backbone. This may promote the hydrophobic interaction between the hydrophobically modified polymer matrix and damaged tissue and/or cell, as discussed throughout the instant specification. It may be understood that the strength of the hydrophobic interaction is based upon the available amount of "hydrophobes" that may interact amongst themselves or one another. Thus, it may further promote the hydrophobic effect by increasing the amount of and/or "hydrophobic" nature of the hydrophobic Tail group that is interacting. For instance, a hydrophobic Tail group, which in its original form may include a hydrocarbon chain, may promote an increase in its hydrophobicity (ability to hydrophobically bond and strength of hydrophic interaction) by having a hydrophobic side chain attach to one of the carbons of its carbon backbone. In a preferred embodiment of the current invention, this may include the attachment of various polycyclic compounds, which may include for instance various steroidal compounds and/or their derivatives such as sterol type compounds, more particularly cholesterol.

In alternative embodiments, the current invention contemplates the use of various molecules and/or compounds that may increase the hydrophobic interaction allowed between the Tail group and the bi-layer membrane of tissues and cells. The side chains may be linear chains, aromatic, aliphatic, cyclic, polycyclic, or any various other types of hydrophobic side chains as contemplated by those skilled in the art. Some of the contemplated hydrophobic side chains may include the following:

I. Linear Alkanes

| Number of C atoms | Formula | Common name | Synonyms |
|---|---|---|---|
| 1 | $CH_4$ | Methane | marsh gas; methyl hydride; natural gas |
| 2 | $C_2H_6$ | Ethane | dimethyl; ethyl hydride; methyl methane |
| 3 | $C_3H_8$ | Propane | dimethyl methane; propyl hydride |
| 4 | $C_4H_{10}$ | n-Butane | butyl hydride; methylethyl methane |
| 5 | $C_5H_{12}$ | n-Pentane | amyl hydride; Skellysolve A |
| 6 | $C_6H_{14}$ | n-Hexane | dipropyl; Gettysolve-B; hexyl hydride; Skellysolve B |
| 7 | $C_7H_{16}$ | n-Heptane | dipropyl methane; Gettysolve-C; heptyl hydride; Skellysolve C |
| 8 | $C_8H_{18}$ | n-Octane | dibutyl; octyl hydride |
| 9 | $C_9H_{20}$ | n-Nonane | nonyl hydride; Shellsol 140 |
| 10 | $C_{10}H_{22}$ | n-Decane | decyl hydride |
| 11 | $C_{11}H_{24}$ | n-Undecane | hendecane |
| 12 | $C_{12}H_{26}$ | n-Dodecane | adakane 12; bihexyl; dihexyl; duodecane |
| 13 | $C_{13}H_{28}$ | nTridecane | |
| 14 | $C_{14}H_{30}$ | n-Tetradecane | |
| 15 | $C_{15}H_{32}$ | n-Pentadecane | |
| 16 | $C_{16}H_{34}$ | n-Hexadecane | cetane |
| 17 | $C_{17}H_{36}$ | n-Heptadecane | |
| 18 | $C_{18}H_{38}$ | n-Octadecane | |
| 19 | $C_{19}H_{40}$ | n-Nonadecane | |
| 20 | $C_{20}H_{42}$ | n-Eicosane | didecyl |
| 21 | $C_{21}H_{44}$ | n-Heneicosane | |
| 22 | $C_{22}H_{46}$ | n-Docosane | |
| 23 | $C_{23}H_{48}$ | n-Tricosane | |
| 24 | $C_{24}H_{50}$ | n-Tetracosane | tetrakosane |
| 25 | $C_{25}H_{52}$ | n-Pentacosane | |
| 26 | $C_{26}H_{54}$ | n-Hexacosane | cerane; hexeikosane |
| 27 | $C_{27}H_{56}$ | n-Heptacosane | |
| 28 | $C_{28}H_{58}$ | n-Octacosane | |
| 29 | $C_{29}H_{60}$ | n-Nonacosane | |
| 30 | $C_{30}H_{62}$ | n-Triacontane | |
| 31 | $C_{31}H_{64}$ | n-Hentraiacontane | untriacontane |
| 32 | $C_{32}H_{66}$ | n-Dotriacontane | dicetyl |
| 33 | $C_{33}H_{68}$ | n-Tritriacontane | |
| 34 | $C_{34}H_{70}$ | n-Tetratriacontane | |
| 35 | $C_{35}H_{72}$ | n-Pentatriacontane | |
| 36 | $C_{36}H_{74}$ | n-Hexatriacontane | |
| 37 | $C_{37}H_{76}$ | n-Heptatriacontane | |
| 38 | $C_{38}H_{78}$ | n-Octatriacontane | |
| 39 | $C_{39}H_{80}$ | n-Nonatriacontane | |
| 40 | $C_{40}H_{82}$ | n-Tetracontane | |
| 41 | $C_{41}H_{84}$ | n-Hentetracontane | |
| 42 | $C_{42}H_{86}$ | n-Dotetracontane | |
| 43 | $C_{43}H_{88}$ | n-Tritetracontane | |
| 44 | $C_{44}H_{90}$ | n-Tetratetracontane | |
| 45 | $C_{45}H_{92}$ | n-Pentatetracontane | |
| 46 | $C_{46}H_{94}$ | n-Hexatetracontane | |
| 47 | $C_{47}H_{96}$ | n-Heptatetracontane | |
| 48 | $C_{48}H_{98}$ | n-Octatetracontane | |
| 49 | $C_{49}H_{100}$ | n-Nonatetracontane | |
| 50 | $C_{50}H_{102}$ | n-Pentacontane | |
| 51 | $C_{51}H_{104}$ | n-Henpentacontane | |
| 52 | $C_{52}H_{106}$ | n-Dopentacontane | |
| 53 | $C_{53}H_{108}$ | n-Tripentacontane | |
| 54 | $C_{54}H_{110}$ | n-Tetrapentacontane | |
| 55 | $C_{55}H_{112}$ | n-Pentapentacontane | |
| 56 | $C_{56}H_{114}$ | n-Hexapentacontane | |
| 57 | $C_{57}H_{116}$ | n-Heptapentacontane | |
| 58 | $C_{58}H_{118}$ | n-Octapentacontane | |
| 59 | $C_{59}H_{120}$ | n-Nonapentacontane | |
| 60 | $C_{60}H_{122}$ | n-Hexacontane | |
| 61 | $C_{61}H_{124}$ | n-Henhexacontane | |
| 62 | $C_{62}H_{126}$ | n-Dohexacontane | |
| 63 | $C_{63}H_{128}$ | n-Trihexacontane | |
| 64 | $C_{64}H_{130}$ | n-Tetrahexacontane | |
| 65 | $C_{65}H_{132}$ | n-Pentahexacontane | |
| 66 | $C_{66}H_{134}$ | n-Hexahexacontane | |
| 67 | $C_{67}H_{136}$ | n-Heptahexacontane | |
| 68 | $C_{68}H_{138}$ | n-Octahexacontane | |
| 69 | $C_{69}H_{140}$ | n-Nonahexacontane | |
| 70 | $C_{70}H_{142}$ | n-Heptacontane | |
| 71 | $C_{71}H_{144}$ | n-Henheptacontane | |
| 72 | $C_{72}H_{146}$ | n-Doheptacontane | |
| 73 | $C_{73}H_{148}$ | n-Triheptacontane | |
| 74 | $C_{74}H_{150}$ | n-Tetraheptacontane | |

-continued

| Number of C atoms | Formula | Common name | Synonyms |
|---|---|---|---|
| 75 | $C_{75}H_{152}$ | n-Pentaheptacontane | |
| 76 | $C_{76}H_{154}$ | n-Hexaheptacontane | |
| 77 | $C_{77}H_{156}$ | n-Heptaheptacontane | |
| 78 | $C_{78}H_{158}$ | n-Octaheptacontane | |
| 79 | $C_{79}H_{160}$ | n-Nonaheptacontane | |
| 80 | $C_{80}H_{162}$ | n-Octacontane | |
| 81 | $C_{81}H_{164}$ | n-Henoctacontane | |
| 82 | $C_{82}H_{166}$ | n-Dooctacontane | |
| 83 | $C_{83}H_{168}$ | n-Trioctacontane | |
| 84 | $C_{84}H_{170}$ | n-Tetraoctacontane | |
| 85 | $C_{85}H_{172}$ | n-Pentaoctacontane | |
| 86 | $C_{86}H_{174}$ | n-Hexaoctacontane | |
| 87 | $C_{87}H_{176}$ | n-Heptaoctacontane | |
| 88 | $C_{88}H_{178}$ | n-Octaoctacontane | |
| 89 | $C_{89}H_{180}$ | n-Nonaoctacontane | |
| 90 | $C_{90}H_{182}$ | n-Nonacontane | |
| 91 | $C_{91}H_{184}$ | n-Hennonacontane | |
| 92 | $C_{92}H_{186}$ | n-Dononacontane | |
| 93 | $C_{93}H_{188}$ | n-Trinonacontane | |
| 94 | $C_{94}H_{190}$ | n-Tetranonacontane | |
| 95 | $C_{95}H_{192}$ | n-Pentanonacontane | |
| 96 | $C_{96}H_{194}$ | n-Hexanonacontane | |
| 97 | $C_{97}H_{196}$ | n-Heptanonacontane | |
| 98 | $C_{98}H_{198}$ | n-Octanonacontane | |
| 99 | $C_{99}H_{200}$ | n-Nonanonacontane | |
| 100 | $C_{100}H_{202}$ | n-Hectane | |
| 101 | $C_{101}H_{204}$ | n-Henihectane | |
| 102 | $C_{102}H_{206}$ | n-Dohectane | |
| 103 | $C_{103}H_{208}$ | n-Trihectane | |
| 104 | $C_{104}H_{210}$ | n-Tetrahectane | |
| 105 | $C_{105}H_{212}$ | n-Pentahectane | |
| 106 | $C_{106}H_{214}$ | n-Hexahectane | |
| 107 | $C_{107}H_{216}$ | n-Heptahectane | |
| 108 | $C_{108}H_{218}$ | n-Octahectane | |
| 109 | $C_{109}H_{220}$ | n-Nonahectane | |
| 110 | $C_{110}H_{222}$ | n-Decahectane | |
| 111 | $C_{111}H_{224}$ | n-Undecahectane | |

II. Cyclic Compounds

Cyclic compounds can be categorized:

| | |
|---|---|
| Alicyclic Compound Cycloalkane Cycloalkene | An organic compound that is both aliphatic and cyclic with or without side chains attached. Typically include one or more all-carbon rings (may be saturated or unsaturated), but NO aromatic character. |
| Aromatic hydrocarbon Polycyclic aromatic hydrocarbon | See above and below |
| Heterocyclic compound | Organic compounds with a ring structure containing atoms in addition to carbon, such as nitrogen, oxygen, sulfur, chloride as part of the ring. May be simple aromatic rings or non-aromatic rings. Some examples are Pyridine (C5H5N), Pyrimidine (C4H4N2) and Dioxane (C4H8O2). |
| Macrocycle | See below. |

III. Polycyclic Compounds—polycyclic compound is a cyclic compound with more than one hydrocarbon loop or ring structures (Benzene rings). The term generally includes all polycyclic aromatic compounds, including the polycyclic aromatic hydrocarbons, the heterocyclic aromatic compounds containing sulfur, nitrogen, oxygen, or another non-carbon atoms, and substituted derivatives of these. The following is a list of some known polycyclic compounds.

| Polycyclic Compounds | Sub-Types | Example Compounds |
|---|---|---|
| Bridged Compound -- compounds which contain interlocking rings | Bicyclo compound | adamantane amantadine biperiden memantine methenamine rimantadine |
| Macrocyclic Compounds -- any molecule containing a ring of seven, fifteen, or any arbitrarily large number of atoms | Calixarene Crown Compounds Cyclodextrins Cycloparaffins Ethers, cyclic Lactams, macrocyclic Macrolides Peptides, cyclic Tetrapyrroles Trichothecenes | |
| Polycyclic Hydrocarbons, Aromatic | Acenaphthenes Anthracenes Azulenes Benz(a)anthracenes Benzocycloheptenes Fluorenes Indenes Naphthalenes Phenalenes Phenanthrenes Pyrenes Spiro Compounds | |
| Steroids | Androstanes Bile Acids and Salts Bufanolides Cardanolides | |

-continued

| Polycyclic Compounds | Sub-Types | Example Compounds |
| --- | --- | --- |
| | Cholanes | |
| | Choestanes | |
| | Cyclosteroids | |
| | Estranes | |
| | Gonanes | |
| | Homosteroids | |
| | Hydroxysteroids | |
| | Ketosteroids | |
| | Norsteroids | |
| | Prenanes | |
| | Secosteroids | |
| | Spirostans | |
| | Steroids, Brominated | |
| | Steroids, Chlorinated | |
| | Steroids, Fluorinated | |
| | Steroids, Heterocyclic | |

The addition of the side chains may increase the stability and strength of the hydrophobic interaction between the Tail group and other hydrophobically active locations, such as a hydrophobic cavity in the bi-layer membrane of various biological structures including tissue and cell membrane structures. This increase in strength and stability may provide further advantages in the ability of the hydrophobically modified polymer matrix to self-assemble, such as providing increased or stabilized rates of reaction in the formation of the network film. The ability to adjust the side chain hydrophobicity may directly impact upon the tertiary and quaternary structure of the hydrophobically modified polymer matrix either as a reactive, solid-state matrix or as a liquid-state solution.

The molecular weight of the polymers comprising the tissue sealant sponge ranges from about 50,000 to about 500,000 grams per gram mole. It is contemplated that the molecular weight of the polymers in the sponge or solution formulations may be less than or greater than the range identified without departing from the scope and spirit of the current invention. For instance, the molecular weight of the polymers comprising the spray ranges from about 10,000 to about 200,000 grams per gram mole. As used herein, the term "molecular weight" means weight average molecular weight. In preferred examples, average molecular weight of polymers is determined by low angle laser light scattering (LLS) and Size Exclusion Chromatography (SEC). In performing low angle LLS, a dilute solution of the polymer, typically 2% or less, is placed in the path of a monochromatic laser. Light scattered from the sample hits the detector, which is positioned at a low angle relative to the laser source. Fluctuation in scattered light over time is correlated with the average molecular weight of the polymer in solution. In performing SEC measurements, again a dilute solution of polymer, typically 2% or less, is injected into a packed column. The polymer is separated based on the size of the dissolved polymer molecules and compared with a series of standards to derive the molecular weight.

The hydrophobically modified polymer spray solution is mixed with a variety of water-soluble reagents which results in faster and more efficient healing of the wound in alternative embodiments of the current invention. A first class of reagents that is mixed with the hydrophobically modified polymer is comprised of those reagents that contribute to the hemostatic integrity of the clot such as for example human thrombin, bovine thrombin, recombinant thrombin, and any of these thrombins in combination with human fibrinogen. Other examples of the first class of reagents include fibrinogen and Factor XIII. A second class of reagents that is mixed with the hydrophobically modified polymer is comprised of those reagents that prevent microbial infection such as norfloxacin, silver, ampicillin and penicillin. Reagents from both classes, e.g. recombinant thrombin and norfloxacin, or reagents from the same class, e.g. recombinant thrombin and fibronectin, may be mixed with the polymer. Various other reagents, catalysts, excipients, transporters, and/or penetrating agents as are known in the art may be employed by the current invention.

In another preferred embodiment of the current invention, the solution of the hydrophobically modified polymer matrix is formulated into a novel adhesive foam. Therefore, the current invention contemplates a method of preparing a foam of the hydrophobically modified polymer matrix. The foam formulation and development techniques employed may vary, including development by standard mechanical agitation means, freeze-dried foam, and various other techniques and formulations as may be contemplated by those of ordinary skill in the art. For instance, the foam may be produced by beating or otherwise agitating the polysaccharide polymer, including the plurality of short hydrophobic substituents, until it foams. It is also contemplated that depending on the polymer being used to prepare the foam, the foaming process takes place in an acidic solution or aqueous base.

It is contemplated that the foaming process may include the introduction of various other materials, such as various gases, into the solution that is being foamed. Different means of mixing the various other gases into the solution to provide a dispersion throughout the solution may be employed. Various foaming agents, modifiers, plasticizers and/or stabilizers may also be employed by the current invention to assist in foaming the solution. For instance, various ionic or non-ionic surfactants, cross-linkers or coagulant stabilizers may be used. It is also further contemplated that the various physical dimensions of and within the foam may be modified and/or controlled by various means as contemplated by those skilled in the art and such means may be employed without departing from the scope and spirit of the current invention.

The various forms of the novel composition of matter provided by the current invention may be used separately and independently. It is also contemplated that these various forms, whether sponge, solution and/or foam, may be employed in combination to provide their beneficial effect. It is also contemplated that one or more the different forms may be mixed and/or blended together for use as a combination product. It is contemplated that the different forms may include similar or different formulations of the novel matrix of the current invention. The interaction of the different forms may be promoted or affected through the use of various different agents as may be contemplated by those of ordinary skill in the art.

Figure 4:
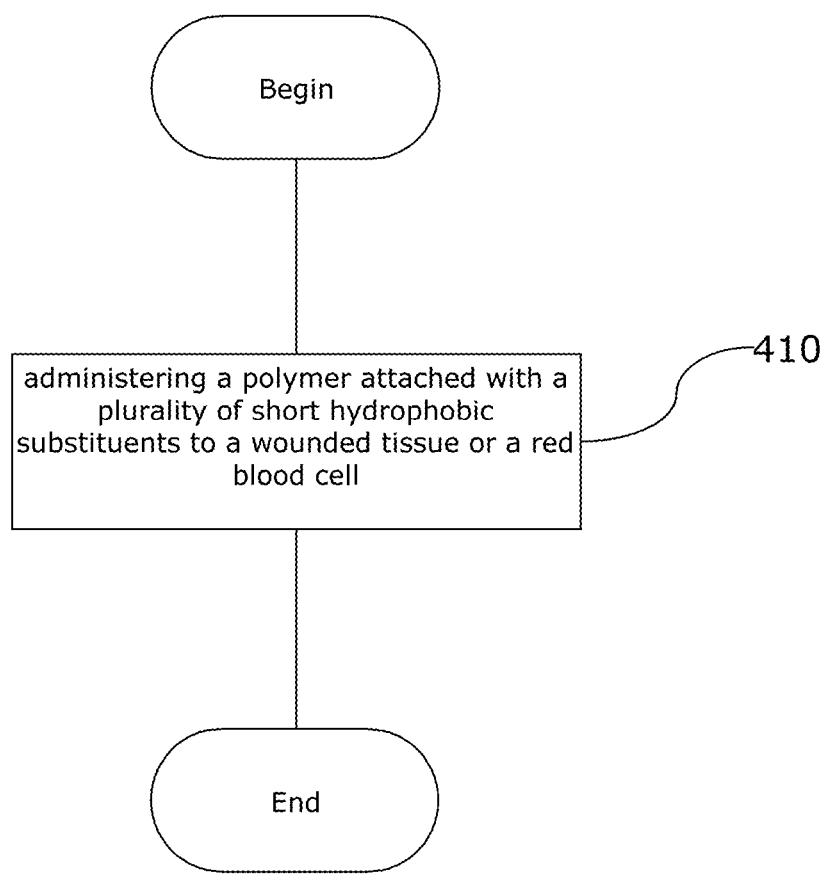
FIG. 4 is a block diagram representation of a method of using the hydrophobically modified biopolymer matrix of the current invention.

In FIG. 4 a method 400 of using a hydrophobically modified biopolymer matrix is provided. The method includes a step 410 of administering a polymer attached with a plurality of short hydrophobic substituent to a wounded tissue or a red blood cell, wherein the attached plurality of short hydrophobic substituent is capable, through hydrophobic interaction, of adhering with the wounded tissue or red blood cell. Administration may preferably occur through directly contacting the polymer matrix with the wounded tissue and/or cells and the application of pressure. The pressure is sustained thereby maintaining contact between the polymer matrix and the wounded tissue and/or cells. It is contemplated that the hydrophobically modified biopolymer matrix is formulated as a solid state sponge that is administered to a wound/damaged tissue by pressing the sponge firmly against a wound area. It is contemplated that the length of time for which pressure is applied may vary, but perhaps most preferably pressure is applied for about 5 to about 10 seconds. The administration of the sponge to the wounded area allows for the interaction between the hydrophobically modified polymer matrix and the damaged tissue. By contacting of the sponge to the damaged tissue the hydrocarbon chains of the plurality of short hydrophobic substituent are able to anchor into the tissue through hydrophobic interaction.

In an alternative embodiment, the hydrophobically modified biopolymer matrix is formulated as an aqueous solution of about 1 to about 2.5% by weight of the polymer. The solution may be administered by spraying it onto a wound area whereby the matrix of the current invention is allowed to hydrophobically interact with the red blood cells and damaged tissue to promote the prevention of blood loss. In either embodiment, sponge or solution, the current invention provides for increased tissue and cellular adhesion which promotes the hemostatic progression in a wounded area.

A method of manufacturing the sponge and/or solution of the current invention is contemplated as an independent method or as a part of the method of using the hydrophobically modified biopolymer matrix, in either the sponge or solution formulation, prior to the administration step. It is contemplated that the sponge is manufactured by dehydrating the hydrophobically modified polymer dissolved in aqueous solution. In a first step, an aqueous liquid solution containing between about 1 and about 2.5% by weight of the hydrophobically modified polymer is cast into a container having the desired dimensions of the sponge. In an example, the container is substantially sealed and frozen in a solution of liquid nitrogen and left in the liquid nitrogen solution for about 20 to about 30 seconds. The container is then opened and placed into a vacuum chamber attached to a freeze drying system which dehydrates the polysaccharide over a period of about 24 hours.

In another example, the container is cast as described above and is placed inside a vacuum oven at about 60° C. for a period of about 48 hours to produce a thin, flexible absorbent film material that is able to be used as a bandage wrap for wounds with extraordinary geometries which are difficult to treat with freeze-dried sponges.

A system of the current invention includes a container that is used to store the solution form of the hydrophobically modified matrix. The container is operationally connected to an ejection mechanism or spray mechanism which is capable of ejecting the solution from the container by means of applying a mechanical pressure to the fluid. The ejection mechanism may be a manual spray mechanism or may provide its functionality through the use of engaging any type of actuator (mechanical, electrical, magnetic, and the like).

In an alternative embodiment of the system, there may be two or more containers wherein a first container stores the solution and a second container stores at least one secondary component like a reagent such as thrombin or norfloxacin, as described above. It is contemplated that the secondary component may be mixed with the hydrophobically modified polymer solution in the same reservoir, or is simultaneously dispensed from a separate chamber. It is further contemplated that the solution and the secondary component may be mixed together prior to ejection. The means used to blend the solution and secondary components may be any such means as contemplated by those of ordinary skill in the art.

The following methods and results provide an exemplary formulation of the matrix of the current invention and its efficacy in promoting hemostasis. It is understood that alternative formulations, such as those explicitly described in the instant specification as well as those that are contemplated by those of ordinary skill in the art, may be used and achieve similar results.

Chitosan was hydrophobically modified in order to increase its adhesion to tissue at the site of injury and to improve its hemostatic properties. Hydrophobes were attached along the backbone of the chitosan polymer. Based on previous work done by Lee et al, the working hypothesis for the present study is that hydrophobes will insert themselves into the bilayers of cells, thus providing chitosan with an added functionality in treating acute wounds. (See J. H. Lee, J. P. Gustin, T. Chen, G. F. Payne and S. R. Raghavan, "Vesicle-biopolymer gels: Networks of surfactant vesicles connected by associating biopolymers." *Langmuir*. (2005), which is herein incorporated by reference in its entirety). If applied to a hemostatic bandage, this property could overcome the primary problem with the HemCon bandage while maintaining the advantages of using chitosan as the base polymer.

Due to these advanced properties of the hm-chitosan, the biopolymer is a viable option for usage as a strongly adhesive hemostatic bandage as well as a flowable spray or surgical sealant to stop minor bleeding and to seal tissues in surgical applications. In this study, the tissue adhesion relative to the level of hydrophobic modification was observed as well as the use of hm-chitosan to gel blood.

Materials and Methods; Hydrophobic Modification of Chitosan; Synthesizing hm-Chitosan Using Dodecaldehyde.

Two grams of chitosan was dissolved in 100 mL of 0.2 M acetic acid by stirring for 30 minutes in a beaker covered with aluminum foil. The solution was filtered using a vacuum filter. Once the chitosan solution was poured from the flask into a 600 mL beaker, 100 mL of ethanol was added to the flask gradually and swirled around to remove the remaining chitosan on the sides of the flask. The ethanol and remaining chitosan was poured into the beaker with the rest of the chitosan. In a separate beaker, 20 mL of ethanol was added to dodecaldehyde (27.9 μL for the 1%, 69.7 μL for the 2.5%, 97.8 μL for the 3.5%, and 167 μL for the 6% modification), which was then slowly poured into the chitosan solution. Sodium cyanoborohydride, 0.78 g, was dissolved in 10 mL of ethanol and added to the chitosan solution. The sodium cyanoborohydride and ethanol solution was added twice more at 2 hour intervals. The mixture was stirred for 24 hours and the hm-chitosan was then precipitated from the solution by adding 0.2 M sodium hydroxide dropwise.

Synthesizing hm-Chitosan Using 4-Octadecyloxybenzaldehyde (2.5% Modification).

The same procedure to modify the chitosan using the dodecaldehyde is used, except 0.1178 g of 4-octadecyloxybenzaldehyde was added instead of the dodecaldehyde. In this study, only a 2.5% modification was made using the 4-octadecyloxybenzaldehyde.

Purification of hm-Chitosan Solutions.

After precipitating the hm-chitosan, the solution was poured into centrifuge tubes, equalized in weight by adding ethanol, and centrifuged at 3,000 rpm for 10 minutes. The supernatant was removed and 20-25 mL of ethanol was added to each tube, stirred using a vortex, and centrifuged again. This process was repeated for a total of three times using ethanol and three additional times using deionized water.

Tissue Adhesion Experiments; Preparation of Films.

After the purification process, the hm-chitosan was removed from the centrifuge tubes into a beaker and an arbitrary amount of 0.2 M acetic acid so that the hm-chitosan was completely submerged. The solution was stirred for 2 hours and then poured into aluminum foil. It was vacuum dried to remove all of the water. Once dry, the hm-chitosan sheets were removed from the foil and dissolved in 0.2 M acetic acid to form a 2 wt % solution. Then 11 g of the hm-chitosan (or chitosan) was dropped into a 2.25" diameter plastic petri dish and left overnight to dry under the hood.

Bovine Tissue Adhesion Tests—by Mass.

The dried films were removed from the petri dishes very carefully to prevent tearing the edges. Each film was cut in half and each piece weighed. All of the films were then further cut and reweighed until all of them were approximately the same weight. The films were then placed on bovine muscle tissue and pressed down gently so that all of the film, except for the raised edges, was in contact with the tissue. For ten minutes, the films were allowed to adhere to the tissue. Then the bovine muscle tissue was inverted and weights were hung sequentially to the edge of the film until it was fully removed from the tissue.

Bovine Tissue Adhesion Tests—by Area.

Once the films were removed from the petri dishes, two rectangles measuring 1.5" by 0.75" each were cut from each film. With the film arranged vertically, a line was measured and drawn 0.5" from the bottom of the film using a thin permanent marker. The films were then placed on bovine muscle tissue so that the line was on the edge of the tissue with the majority of the film adhered to the tissue and the 0.5" by 0.75" rectangle hanging off the side. After being pressed gently into the tissue, the films were left to adhere to the tissue for ten minutes. The bovine muscle tissue was then held vertically so the films were perpendicular to the floor with the unattached portion of the film on the bottom. Weights were hung sequentially to the films until they were completely peeled from the tissue.

Texture Analyzer.

A TA.XT2i Texture Analyzer with a 5 kg load cell was used to perform this set of experiments. The instrument was set to the compression test mode. Small viles were filled approximately half full with 2 wt % solutions of hm-chitosan of varying levels of modification as well as the unmodified chitosan. A ½" diameter cylindrical probe was attached and aligned with the vile of solution. The settings were applied with a pre-test speed of 3 mm/s, a test speed of 2 mm/s, and a post test speed of 1 mm/s. The target mode was distance and the distance the probe traveled after touching the surface of the solution was set to 2 mm. As the probe was lowered into the vile, the force on the probe when it came in contact with the solution triggered the instrument to record the data. The resulting graphs produced were then used to calculate the adhesion of each solution.

Blood Gelling Experiments; Initial Blood Gelling Tests.

When the human blood was drawn, it was put into test tubes whose interior walls were lined with heparin. A pipette was then used to measure out 1 mL of blood, which was relocated to another test tube. Another pipette was used to add 1 mL of the chitosan (or hm-chitosan) to the blood. During the experiments, the 1%, 2.5%, and 3.5% modified hm-chitosan (modified using dodecaldehyde) was used as well as 2.5% modified hm-chitosan that was modified with the 4-octadecyloxybenzaldehyde. The time that it took for the mixture to gel was observed and recorded.

Rheology of Blood and Chitosan Solution.

A AR2000 advanced rheometer with a cone and plate geometry was used to measure the dynamic viscoelastic properties for these experiments. The cone had a 40 mm diameter with a 2 degree angle. In order to ensure that all the measurements were within the linear viscoelastic regions, first stress amplitude sweeps were performed. After the human blood was drawn into the test tubes with the heparin, a pipette was used to add 1 mL of blood onto the plate of the rheometer. Then 1 mL of the chitosan (or hm-chitosan) solution was added to the blood on the plate. Once the solutions were combines, the parameters for the rheometer were set up and the run was started. The cone lowered into contact with the solution and a sinusoidal strain was subjected to the subject with increasing frequency of oscillations. The elastic and viscous moduli were obtained over the frequency range of 0.01 to 10 Hz. Dynamic rheology experiments were performed using unmodified chitosan, 2.5% and 6% modified hm-chitosan (modified using dodecaldehyde), and 2.5% modified hm-chitosan modified using 4-octadecyloxybenzaldehyde.

Results and Discussion; Tissue Adhesion Experiments; Texture Analyzer.

In comparison of the varying hm-chitosan solutions, an obvious relationship was not observed in the relative adhesion calculations found using the texture analyzer. As shown in Table 1 below, the 1% and 3.5% modified hm-chitosan had the highest level of adhesion while the unmodified chitosan was the least adhesive.

TABLE 1

Adhesion of hm-Chitosan Solutions - Texture Analyzer

| | Level of Modification | | | |
|---|---|---|---|---|
| | 0% | 1% | 2.5% | 3.5% |
| Adhesion (g · sec) | 3.126 | 3.409 | 3.200 | 3.404 |

The difference between the highest level of adhesion (1% modification) and the lowest (0% modification) was 0.278 g·sec. The adhesion calculations found does not show a trend with the increasing level of modification with the 2.5% modified hm-chitosan being lower than the 1% and 3.5%; however, with the unmodified chitosan having the lowest adhesion, the data indicates that the hydrophobic modification of the chitosan does increase the adhesion of the solution.

Bovine Muscle Tissue; Standardized Film Weight.

Figure 5:
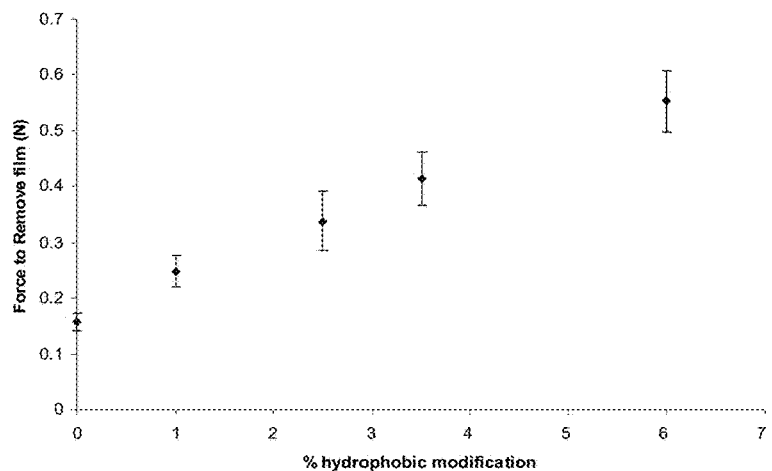
FIG. 5 is a graph showing the Force required for removal of chitosan and hm-chitosan films vs. level of hydrophobic modification.

The experiments in which the chitosan and hm-chitosan films were adhered to bovine muscle tissue and removed by sequentially hanging weights from the inverted tissue were repeated several times. As shown in FIG. 5, the average force to needed to remove the films increased nearly linearly with the increasing level of hydrophobic modification. The standard deviation of force for each level of modification is fairly low with a high of 0.056 N. This precision in data significantly contributes to the credibility of the relationship between the adhesion and modification level.

In unmodified chitosan, the high adhesion to tissue is due to an electrostatic attraction between cationic chitosan and anionic cell surfaces. As previously mentioned, it is hypothesized that the increase in adhesion with increasing hydrophobic modification is due to the anchoring of the hydrophobes on the backbone of the chitosan into the bilayer of the tissue cells. In this study, the highest level of modification tested is 6% modified using dodecaldehyde, and this hm-chitosan produced the greatest adhesion to the bovine muscle tissue. Due to the hydrophobic nature of the modification, a percentage of modification higher than 6% would be difficult to dissolve into solution which would make it unusable in this study.

Though the results of the experiments provide a nearly linear relationship between the adhesion and the level of hydrophobic modification, the actual measurements of the force necessary to remove the films is negligible and the main focus is on the relationship. In this adhesion experiment, the standardization was administered by equalizing the weights of the films and by adhering all levels of modification to the same piece of bovine muscle tissue. With this method of standardization, the films were of varying surface area and thickness which could have had an affect on the adhesion.

Standardized Area of Contact Between Film and Tissue.

To vary the method of standardization of the films, additional adhesion experiments were performed using films with the same surface area in contact with the bovine muscle tissue. The films measured 0.75" by 1.5" with the portion in contact with the tissue measuring 0.75" by 1.00".

dodecaldehyde and b) 4-octadecyloxybenzaldehyde. The dodecaldehyde has a 12 carbon chain while the 4-octadecyloxybenzaldehyde has an 18 carbon chain connected to an oxygen atom that is bonded to a benzene ring. Whether or not the increased adhesion is due to the increase in carbon chain length or in the addition of the benzene ring is unknown, and this is a topic of interest for future experiments in this study.

This series of experiments differs significantly from the other bovine muscle tissue adhesion experiment in terms of standardization in addition to the forces involved. With the inversion of the tissue in the other set of experiments, the films were pulled at a 90 degree angle. In these experiments, the tissue was held vertically and the films were pulled along the direction of the alignment of the tissue. Due to this setup, the force needed to remove the films was higher since there was a shear force involved in the removal and the experiment was actually a type of static load shear holding test.

Since the surface area of the films was equalized in these experiments, the weight and thickness of the films varied. Similarly to the other adhesion experiments, the same piece of bovine muscle tissue was used for each trial in order to reduce variation due to the properties of the tissue.

TABLE 2

Weight required to remove the films of varying levels of hydrophobic modification

| | 0% | 1% | 2.5% | 3.5% | 6% | 2.5% (C18) |
|---|---|---|---|---|---|---|
| Trial 1 | 78.6451 g | 50.6870 g | 175.8375 g | 104.4592 g | 82.0132 g | 249.0300 g |
| Trial 2 | 104.2906 g | 112.8136 g | 129.0033 g | 144.4069 g | 118.2246 g | 171.9973 g |

In addition to the five levels of modification of the hm-chitosan modified using dodecaldehyde that were used in the previous bovine muscle tissue adhesion experiments, a film composed of 2.5% modified solution of hm-chitosan that was modified using 4-octadecyloxybenzaldehyde was also used. As shown in Table 2, the 2.5% 4-octadecyloxybenzaldehyde modified hm-chitosan films required the greatest amount of force for removal which was notably higher than the amount required for the second most adhesive film. As the first experiment to test the adhesion of the 4-octadecyloxybenzaldehyde modified hm-chitosan film, the results suggest that this modification causes an even higher increase in adhesive properties.

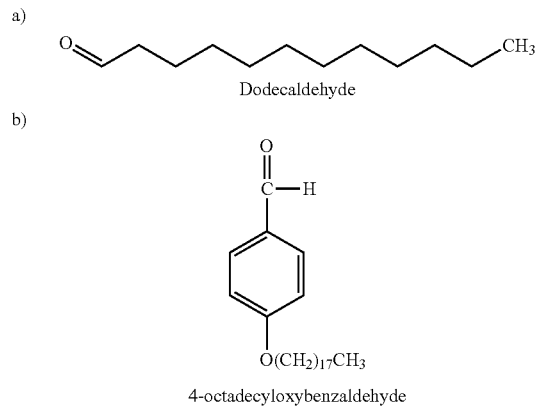

Shown above are the chemical structures and names of the two aldehydes used for the modification of the chitosan: a)

Blood Gelling Experiments; Initial Blood Gelling—Qualitative Data.

In the blood gelling experiments, the blood that was drawn was mixed with heparin which is an anticoagulant. The purpose of adding the heparin was to ensure that the change in blood viscosity and the blood gellation was due to the addition of the hm-chitosan solutions and not a result of the natural blood coagulation process. In the initial experiments, it was observed that the addition of unmodified chitosan to blood did not have a visually apparent increase in viscosity. The mixture was very fluidic and immediately flowed when the test tube was inverted. The blood, when mixed with 1%, 2.5%, and 3.5% modified hm-chitosan, became exceptionally viscous, though never gelled completely. A gel is characterized as a solution of infinite viscosity, and does not flow even when inverted in a test tube. In this experiment, the 1%, 2.5%, and 3.5% modified hm-chitosan, when mixed with blood, became so viscous that the solutions could remain intact for several seconds when the test tube was inverted; however, after a few seconds, the solutions slowly flowed down the side.

Figure 6A:
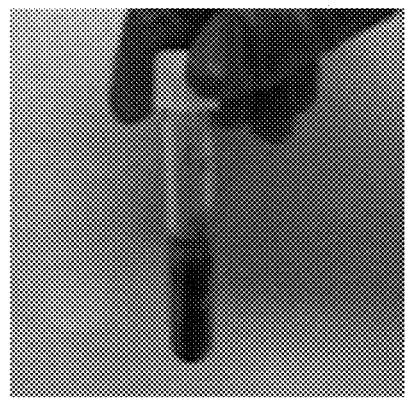
FIG. 6A is an illustration of 4-octadecyloxybenzaldehyde 2.5% modified hm-chitosan and blood solution when first mixed.
Figure 6B:
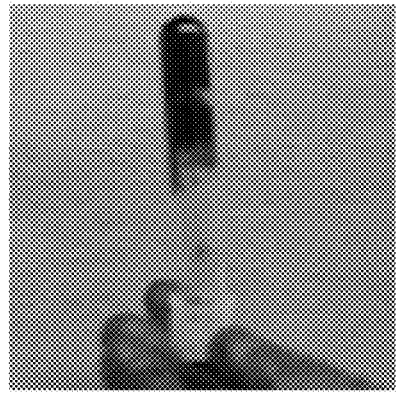
FIG. 6B is an illustration of -octadecyloxybenzaldehyde 2.5% modified hm-chitosan and blood solution immediately after mixture with inverted test tube to show gelation of solution.
Figure 7A:
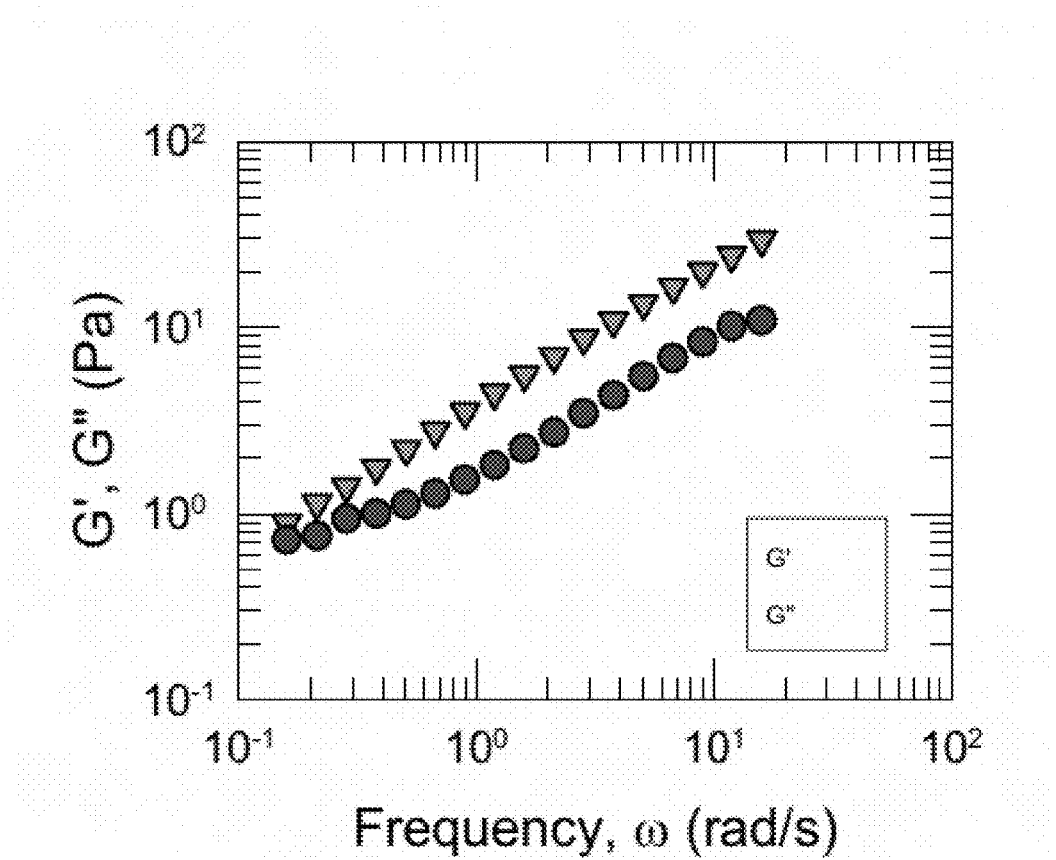
FIG. 7A is an illustration of a dynamic rheology frequency sweep showing a chitosan (0.75 wt %)+blood (heparinized).
Figure 7B:
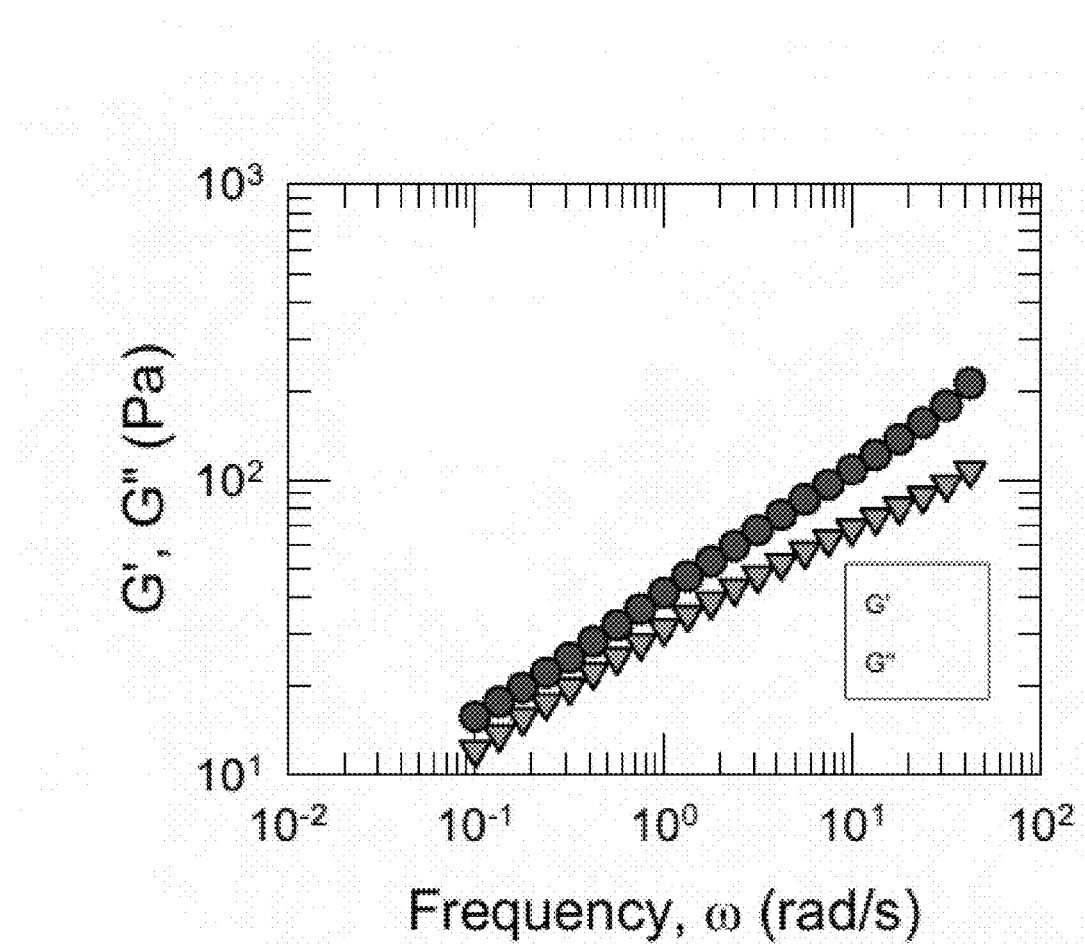
FIG. 7B is an illustration of a dynamic rheology frequency sweep showing 2.5% C12 mod hm-chitosan (0.75 wt %)+blood (heparinized).
Figure 7C:
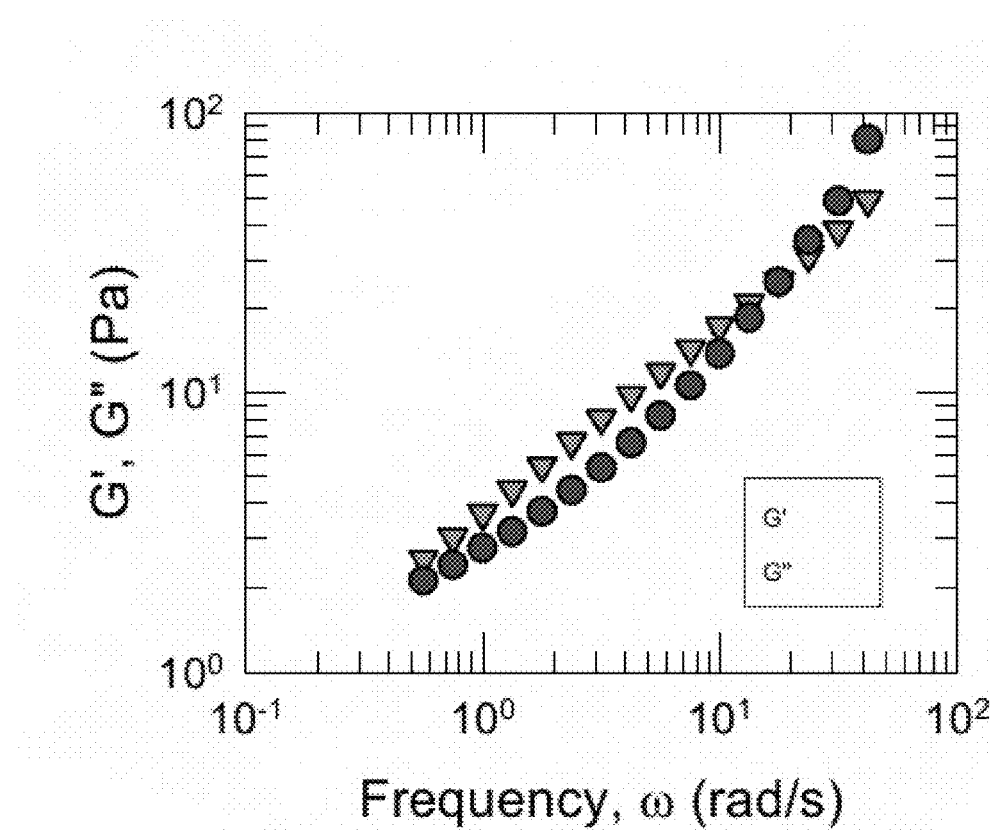
FIG. 7C is an illustration of a dynamic rheology frequency sweep showing 6% C12 mod hm-Chitosan (0.75 wt %)+blood (heparinized).
Figure 7D:
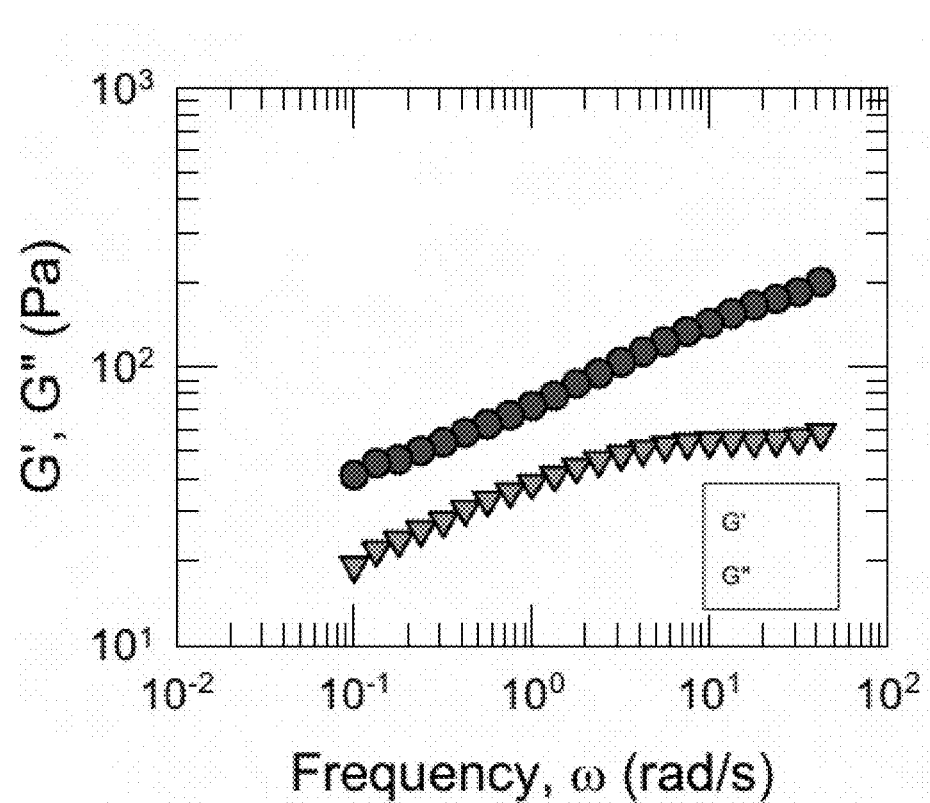
FIG. 7D is an illustration of a dynamic rheology frequency sweep showing 2.5% mod (C18-benz) hm-Chitosan (0.4 wt %)+blood (heparinized).
Figure 8A:
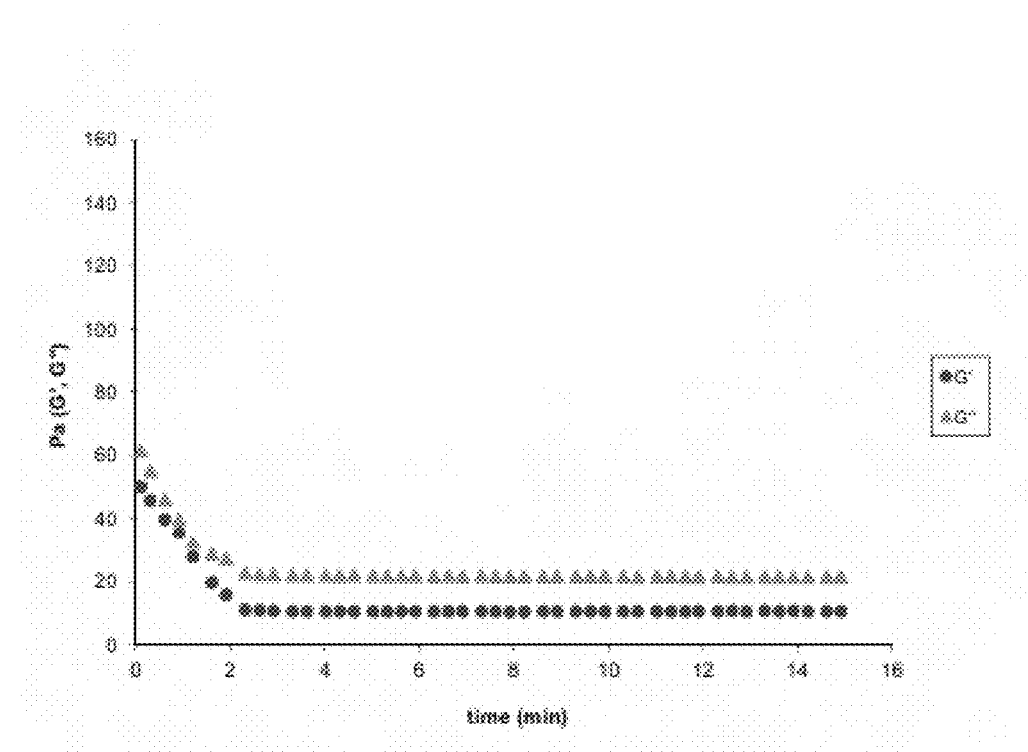
FIG. 8A is an illustration of time to gelation showing a chitosan (0.75 wt %)+blood (heparinized).
Figure 8B:
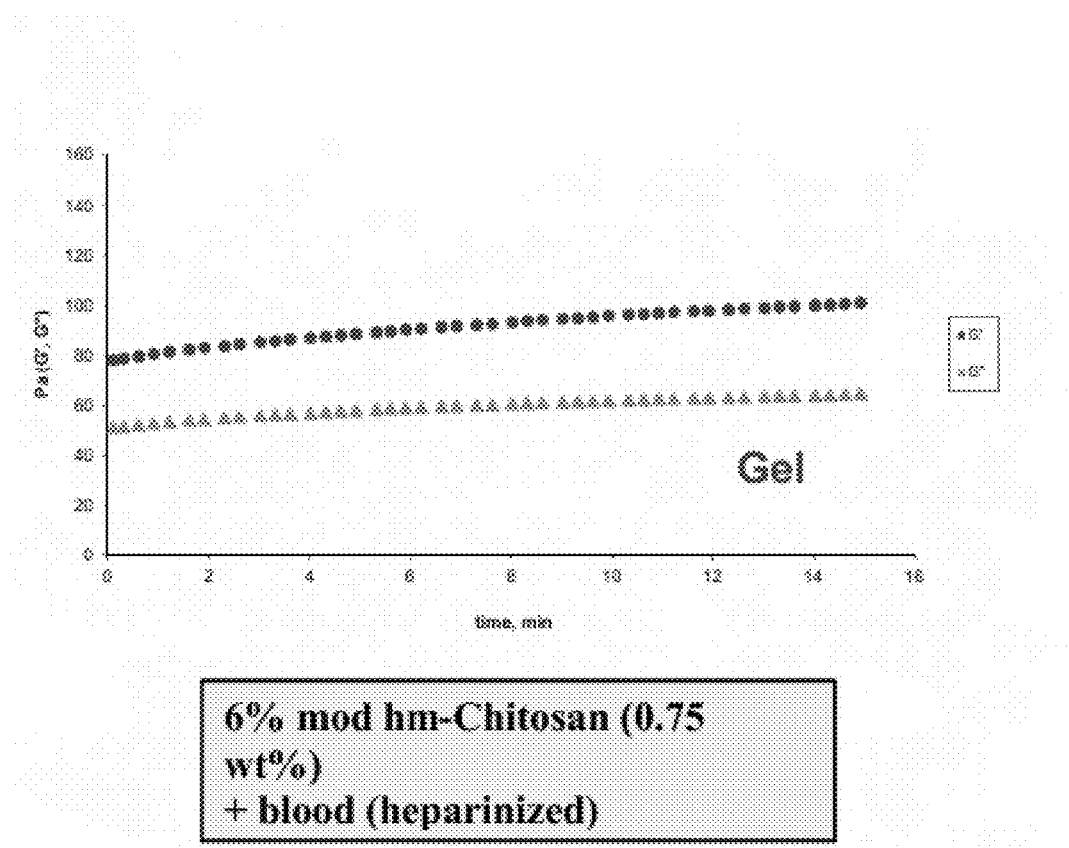
FIG. 8B is an illustration of time to gelation showing 2.5% C12 mod hm-chitosan (0.75 wt %)+blood (heparinized).
Figure 8C:
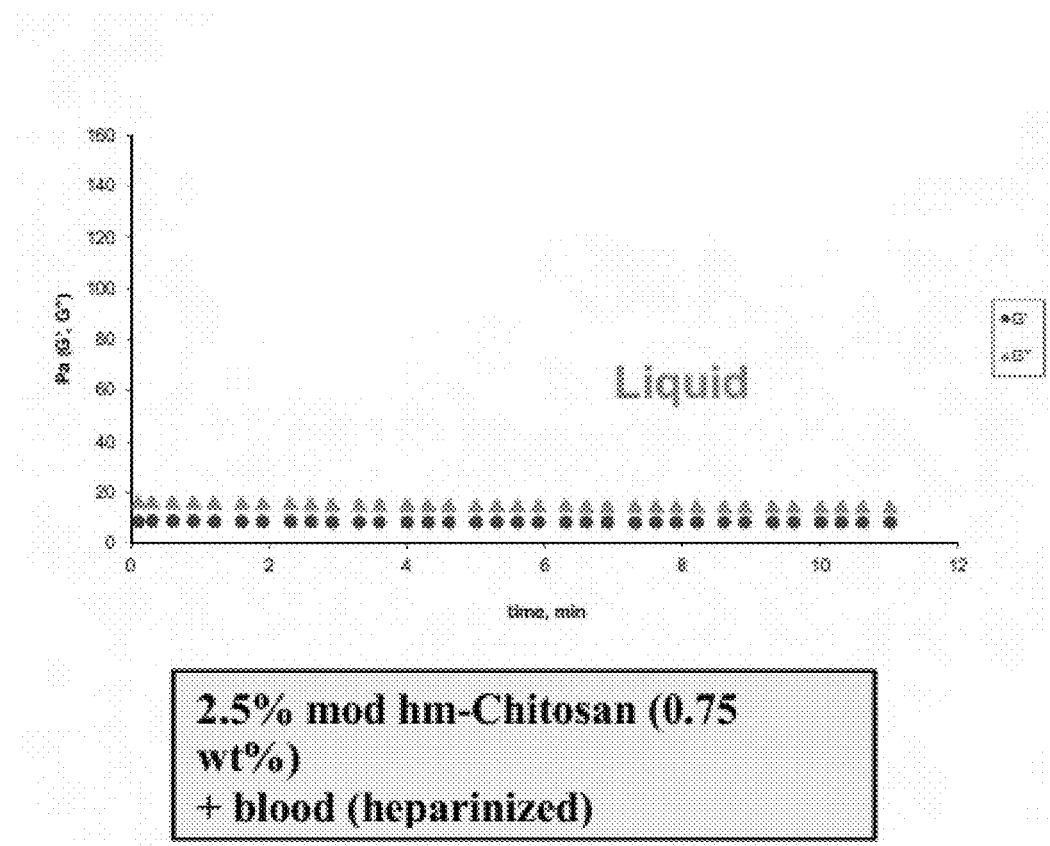
FIG. 8C is an illustration of time to gelation showing 6% C12 mod hm-Chitosan (0.75 wt %)+blood (heparinized).
Figure 8D:
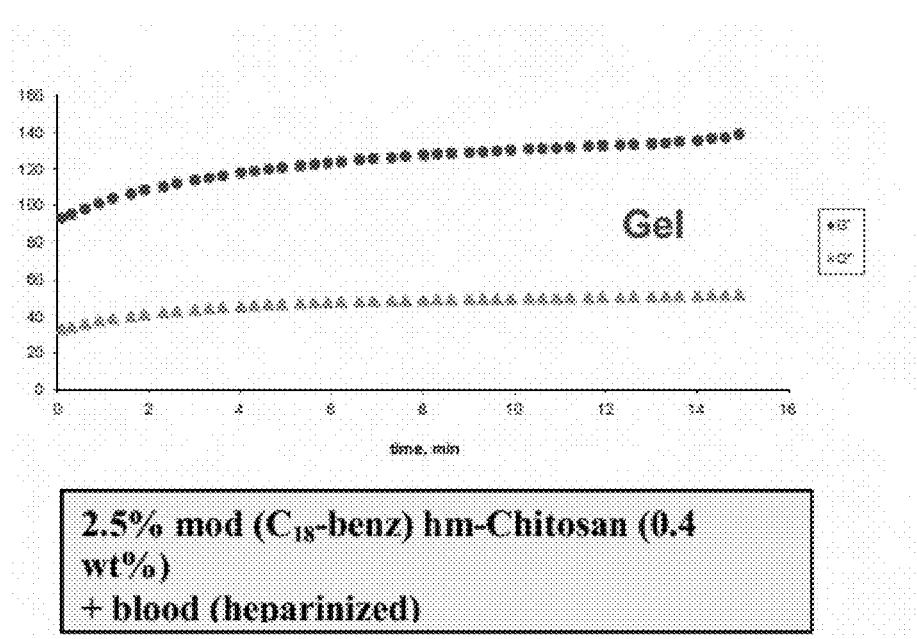
FIG. 8D is an illustration of time to gelation showing 2.5% mod (C18-benz) hm-Chitosan (0.4 wt %)+blood (heparinized).

The 2.5% hm-chitosan solution that was modified using the 4-octadecyloxybenzaldehyde completely gelled the blood almost instantaneously (less than 30 seconds) after being added. FIG. 6 shows a photo of the 2.5% modified hm-chitosan, modified using 4-octadecyloxybenzaldehyde, mixed with the blood in a test tube and then another photo of the test tube completely inverted. The gelled solution remains in the bottom of the inverted test tube. The instantaneous gellation of the blood by the 2.5% modified hm-chitosan, modified using 4-octadecyloxybenzaldehyde, is a significant characteristic and has promising future applications as a medical spray or surgical sealant.

Rheology of Blood and hm-Chitosan; Frequency Sweep.

The qualitative observations obtained in the initial blood gelling experiments were further quantified using an advanced rheometer. Dynamic rheology experiments ultimately yield plots of G' (elastic modulus) and G" (viscous modulus) as functions of frequency which are collectively called the frequency spectrum of the material. For our purposes of quantitatively defining the solutions of chitosan and blood as viscous or elastic, the graphs shown in FIG. 7, identify each solution as liquid or gel (solid) form. For the unmodified chitosan and the 2.5% modified hm-chitosan modified using dodecaldehyde, the results show that the viscous modulus is higher than the elastic modulus. In general terms, this data indicates that the solutions have stronger viscous properties than elastic and remain in liquid form. The graph of the 2.5% modified hm-chitosan (dodecaldehyde) seems to show some visco-elastic properties with the intersection of the elastic and viscous modulous; however, for our purposes the viscous modulus is higher than the elastic modulus over most of the frequency range and only shows elastic behavior at high frequencies.

Both the graphs of the 6% modified hm-chitosan (dodecaldehyde) and the 2.5% modified hm-chitosan (4-octadecyloxybenzaldehyde) quantifies the solutions as gels since the elastic modulus remains above the viscous modulus throughout the frequency range. With the dodecaldehyde 6% modified hm-chitosan and blood solution, the moduli are closer together than the 4-octadecyloxybenzaldehyde 2.5% modified hm-chitosan and blood solution. This suggests that the elastic properties of the 4-octadecyloxybenzaldehyde 2.5% modified hm-chitosan and blood solution are more dominant than with the dodecaldehyde 6% modified hm-chitosan.

Dynamic Rheology—Time to Gellation.

The previous frequency sweep graphs quantitatively show that blood, when mixed with two of the hm-chitosan solutions, form gels; however, the primary factor for these solutions applicability as liquid medical sprays or surgical sealants lies within the time of gellation after the blood and hm-chitosan solutions mix. As shown in FIG. 8, the hm-chitosan and blood solutions experience negligible variation with time after the initial mixture. For both the blood and unmodified chitosan and the blood and 2.5% modified hm-chitosan (dodecaldehyde) solutions that remained in liquid form, the elastic modulus and viscous modulus remain relatively constant over time. One unexplainable anomaly in the data is shown in the graph of the unmodified chitosan and blood solution with the initial nearly linear decrease in moduli. This is believed to be a result of an instrumental malfunction rather than a representation of the visco-elastic response of the solution; however, even with the initial decrease, the moduli quickly level out and remains constant with time.

In this experiment, the blood and hm-chitosan solutions are mixed together and the cone of the advanced rheometer immediately lowers into the solution and begins the oscillations of low frequency. As shown above in the graphs of the 6% modified hm-chitosan (dodecaldehyde) and the 2.5% modified hm-chitosan (4-octadecyloxybenzaldehyde) and blood solutions, the elastic modulus is higher than the viscous modulus for the first measurement which is determined only seconds after the solutions are mixed. This data corresponds with the initial blood gelling experiment results in showing the gellation time of only a few seconds. With nearly instantaneous gellation when it comes in contact with blood, the application of hm-chitosan liquid solutions could potentially mean a significant advancement in surgical sealants and sprays.

CONCLUSION

The motivation behind this study was to develop a new material with advanced properties for use as a hemostatic bandage for acute wounds and as a flowable spray or surgical sealant to stop minor bleeding and to seal tissues in surgical procedures. With our hydrophobic modification of chitosan using dodecaldehyde and 4-octadecyloxybenzaldehyde, the experiments of this study focused on the impact of the modification on tissue adhesion in addition to the polymers interaction with blood. In the tissue adhesion experiments, it was concluded that tissue adhesiveness increases proportionally with the level of hydrophobic modification on the chitosan backbone. The experiments on the interaction of the modified chitosan with blood revealed that the 6% dodecaldehyde modified hm-chitosan and the 4-octadecyloxybenzaldehyde 2.5% modified hm-chitosan instantly forms a gel when mixed with blood. With these results showing the impact of the hydrophobic modification of chitosan in terms of tissue adhesion and interaction with blood, hm-chitosan has advanced qualities which give it a promising future as a hemostatic bandage and surgical sealant.

It is believed that the present invention and many of its attendant advantages will be understood by the forgoing description. It is also believed that it will be apparent that various changes may be made in the form, construction and arrangement of the components thereof without departing from the scope and spirit of the invention or without sacrificing all of its material advantages. The form herein before described being merely an explanatory embodiment thereof. It is the intention of the following claims to encompass and include such changes.

What is claimed is:

1. A method, comprising:
applying a hydrophobically modified biopolymer to a bleeding wound, wherein hydrophobic moieties comprising a hydrocarbon group having at least eight and no more than eighteen carbon atoms are covalently attached along the biopolymer backbone and wherein the modified biopolymer creates an artificial clot when exposed to blood, and wherein the biopolymer is selected from chitosans and alginates.

2. The method of claim 1, wherein the hydrophobically modified biopolymer is present in a solution having a concentration of the biopolymer of about 1% to about 2.5% by weight relative to the total weight of the solution of the biopolymer.

3. The method of claim 1, wherein the hydrophobic moieties are covalently attached to as many as 10% of available amines of chitosan.

4. The method of claim 1, wherein the biopolymer is a chitosan salt.

5. The method of claim 4, wherein the chitosan salt is selected from the group consisting of chitosan lactate, chitosan salicylate, chitosan pyrrolidone carboxylate, chitosan itaconate, chitosan niacinate, chitosan formate, chitosan gallate, chitosan glutamate, chitosan maleate, chitosan aspartate, and chitosan glycolate.

6. The method of claim 1, wherein the modified biopolymer self-assembles to create an artificial clot.

7. The method of claim 1, wherein the modified biopolymer provides for tissue adhesion and cellular adhesion to create an artificial clot.

8. The method of claim 1, wherein the modified biopolymer binds to negatively charged surfaces.

9. The method of claim 3, wherein the chitosan has a level of deacetylation of from 60% to 100%.

10. The method of claim 9, wherein the hydrophobic moieties occur between 1.5 and 4.5% of available amines along the backbone.

11. A method, comprising:
applying a hydrophobically modified chitosan to a bleeding wound, wherein hydrophobic moieties comprising a hydrocarbon group having from eight to eighteen carbon atoms are covalently attached along the chitosan backbone at up to 10% of available amines, and the chitosan has a degree of deacetylation of from 60 to 100%, and wherein the hydrophobically modified chitosan creates an artificial clot when exposed to blood.

12. The method of claim 11, wherein the hydrophobically modified chitosan is present in a solution having a concentration of the biopolymer of about 1% to about 2.5% by weight relative to the total weight of the solution of the hydrophobically modified chitosan.

* * * * *